(12) United States Patent
Dayton et al.

(10) Patent No.: US 12,161,371 B2
(45) Date of Patent: Dec. 10, 2024

(54) CONTOURED BONE PLATE WITH LOCKING SCREW FOR BONE COMPRESSION, PARTICULARLY ACROSS A TARSOMETATARSAL JOINT

(71) Applicant: Treace Medical Concepts, Inc., Ponte Vedra, FL (US)

(72) Inventors: Paul Dayton, Ankeny, IA (US); Daniel Hatch, Greeley, CO (US); Jason May, St. John's, FL (US); Sean Scanlan, Jacksonville, FL (US); Joe Ferguson, Ponte Vedra Beach, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 232 days.

(21) Appl. No.: 17/577,202

(22) Filed: Jan. 17, 2022

(65) Prior Publication Data
US 2022/0226028 A1 Jul. 21, 2022

Related U.S. Application Data

(60) Provisional application No. 63/138,726, filed on Jan. 18, 2021.

(51) Int. Cl.
*A61B 17/80* (2006.01)
*A61B 17/56* (2006.01)
(Continued)

(52) U.S. Cl.
CPC ...... *A61B 17/8014* (2013.01); *A61B 17/8057* (2013.01); *A61B 17/8061* (2013.01);
(Continued)

(58) Field of Classification Search
CPC ............ A61B 17/8014; A61B 17/8057; A61B 17/8085; A61B 17/8061; A61B 17/863;
(Continued)

(56) References Cited

U.S. PATENT DOCUMENTS

| | | | |
|---|---|---|---|
| 3,664,022 A | 5/1972 | Small | |
| 4,069,824 A | 1/1978 | Weinstock | |

(Continued)

FOREIGN PATENT DOCUMENTS

| | | |
|---|---|---|
| AU | 2009227957 B2 | 7/2014 |
| CA | 2491824 A1 | 9/2005 |

(Continued)

OTHER PUBLICATIONS

Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.

(Continued)

*Primary Examiner* — Marcela I. Shirsat
(74) *Attorney, Agent, or Firm* — Fredrikson & Byron, P.A.

(57) ABSTRACT

A method of applying a bone plate across a tarsometatarsal joint or two different portions of a metatarsal may involve positioning a bone plate across a separation between two bone portions. The bone plate can have at least two fixation holes and a bend between the holes. A locking screw can be inserted through one or both holes that has a head thread and a shaft thread, where the shaft thread has a pitch greater than a pitch of the head thread. The locking screw can be screwed into an underlying bone portion until the bend in the bone plate is deformed.

32 Claims, 18 Drawing Sheets

(51) Int. Cl.
*A61B 17/68* (2006.01)
*A61B 17/84* (2006.01)
*A61B 17/86* (2006.01)
*A61B 17/88* (2006.01)

(52) U.S. Cl.
CPC ...... *A61B 17/863* (2013.01); *A61B 2017/564* (2013.01); *A61B 2017/681* (2013.01); *A61B 17/8004* (2013.01); *A61B 17/8052* (2013.01); *A61B 17/8085* (2013.01); *A61B 17/848* (2013.01); *A61B 17/8863* (2013.01)

(58) Field of Classification Search
CPC ............ A61B 17/8863; A61B 17/1728; A61B 17/848; A61B 17/80; A61B 17/8004; A61B 17/8052; A61B 17/808; A61B 17/8605; A61B 17/58; A61B 2017/564; A61B 2017/681
USPC ....... 606/281, 282, 286, 283, 284, 291, 301, 606/305, 317, 86 B
See application file for complete search history.

(56) References Cited

U.S. PATENT DOCUMENTS

| | | |
|---|---|---|
| 4,159,716 A | 7/1979 | Borchers |
| 4,187,840 A | 2/1980 | Watanabe |
| 4,335,715 A | 6/1982 | Kirkley |
| 4,338,927 A | 7/1982 | Volkov et al. |
| 4,349,018 A | 9/1982 | Chambers |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,627,425 A | 12/1986 | Reese |
| 4,628,919 A | 12/1986 | Clyburn |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,895,141 A | 1/1990 | Koeneman et al. |
| 4,952,214 A | 8/1990 | Comparetto |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| 5,254,119 A | 10/1993 | Schreiber |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,413,579 A | 5/1995 | Du Toit |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barrett et al. |
| 5,601,565 A | 2/1997 | Huebner |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,667,510 A | 9/1997 | Combs |
| H1706 H | 1/1998 | Mason |
| 5,722,978 A | 3/1998 | Jenkins |
| 5,749,875 A | 5/1998 | Puddu |
| 5,779,709 A | 7/1998 | Harris et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,022,352 A | 2/2000 | Vandewalle |
| 6,027,504 A | 2/2000 | McGuire |
| 6,030,391 A | 2/2000 | Brainard et al. |
| 6,162,223 A | 12/2000 | Orsak et al. |
| 6,171,309 B1 | 1/2001 | Huebner |
| 6,203,545 B1 | 3/2001 | Stoffella |
| 6,248,109 B1 | 6/2001 | Stoffella |
| 6,391,031 B1 | 5/2002 | Toomey |
| 6,416,465 B2 | 7/2002 | Brau |
| 6,478,799 B1 | 11/2002 | Williamson |
| 6,511,481 B2 | 1/2003 | von Hoffmann et al. |
| 6,547,793 B1 | 4/2003 | McGuire |
| 6,676,662 B1 | 1/2004 | Bagga et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,796,986 B2 | 9/2004 | Duffner |
| 6,859,661 B2 | 2/2005 | Tuke |
| 7,018,383 B2 | 3/2006 | McGuire |
| 7,033,361 B2 | 4/2006 | Collazo |
| 7,037,309 B2 | 5/2006 | Weil et al. |
| 7,097,647 B2 | 8/2006 | Segler et al. |
| 7,112,204 B2 | 9/2006 | Justin et al. |
| 7,153,310 B2 | 12/2006 | Ralph et al. |
| 7,182,766 B1 | 2/2007 | Mogul |
| 7,229,445 B2 | 6/2007 | Hayeck et al. |
| 7,241,298 B2 | 7/2007 | Nemec et al. |
| 7,282,054 B2 | 10/2007 | Steffensmeier et al. |
| 7,377,924 B2 | 5/2008 | Raistrick et al. |
| 7,465,303 B2 | 12/2008 | Riccione et al. |
| 7,540,874 B2 | 6/2009 | Trumble et al. |
| 7,572,258 B2 | 8/2009 | Stiernborg |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,763,026 B2 | 7/2010 | Egger et al. |
| D629,900 S | 12/2010 | Fisher |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,083,746 B2 | 12/2011 | Novak |
| 8,123,753 B2 | 2/2012 | Poncet |
| 8,137,406 B2 | 3/2012 | Novak et al. |
| 8,147,530 B2 | 4/2012 | Strnad et al. |
| 8,167,918 B2 | 5/2012 | Strnad et al. |
| 8,172,848 B2 | 5/2012 | Tomko et al. |
| 8,177,820 B2 | 5/2012 | Anapliotis et al. |
| 8,192,441 B2 | 6/2012 | Collazo |

(56) References Cited

U.S. PATENT DOCUMENTS

| | | |
|---|---|---|
| 8,197,487 B2 | 6/2012 | Poncet et al. |
| 8,231,623 B1 | 7/2012 | Jordan |
| 8,231,663 B2 | 7/2012 | Kay et al. |
| 8,236,000 B2 | 8/2012 | Ammann et al. |
| 8,246,561 B1 | 8/2012 | Agee et al. |
| D666,721 S | 9/2012 | Wright et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plassky et al. |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Buescher |
| 8,382,807 B2 | 2/2013 | Austin et al. |
| 8,403,966 B2 | 3/2013 | Ralph et al. |
| D679,395 S | 4/2013 | Wright et al. |
| 8,409,209 B2 | 4/2013 | Ammann et al. |
| 8,435,246 B2 | 5/2013 | Fisher et al. |
| 8,475,462 B2 | 7/2013 | Thomas et al. |
| 8,496,662 B2 | 7/2013 | Novak et al. |
| 8,496,690 B2 | 7/2013 | Sixto et al. |
| 8,518,045 B2 | 8/2013 | Szanto |
| 8,523,870 B2 | 9/2013 | Green, II et al. |
| 8,529,571 B2 | 9/2013 | Horan et al. |
| 8,540,777 B2 | 9/2013 | Ammann et al. |
| 8,545,508 B2 | 10/2013 | Collazo |
| D694,884 S | 12/2013 | Mooradian et al. |
| D695,402 S | 12/2013 | Dacosta et al. |
| 8,632,545 B2 | 1/2014 | Sarangapani et al. |
| 8,652,142 B2 | 2/2014 | Geissler |
| 8,657,820 B2 | 2/2014 | Kubiak et al. |
| D701,303 S | 3/2014 | Cook |
| 8,672,945 B2 | 3/2014 | Lavallee et al. |
| 8,696,716 B2 | 4/2014 | Kartalian et al. |
| 8,702,715 B2 | 4/2014 | Ammann et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,771,279 B2 | 7/2014 | Philippon et al. |
| 8,777,948 B2 | 7/2014 | Bernsteiner |
| 8,777,998 B2 | 7/2014 | Daniels et al. |
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,828,063 B2 | 9/2014 | Blitz et al. |
| 8,858,602 B2 | 10/2014 | Weiner et al. |
| 8,882,778 B2 | 11/2014 | Ranft |
| 8,882,816 B2 | 11/2014 | Kartalian et al. |
| 8,888,785 B2 | 11/2014 | Ammann et al. |
| 8,888,824 B2 | 11/2014 | Austin et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,940,026 B2 | 1/2015 | Hilse et al. |
| 8,945,132 B2 | 2/2015 | Plassy et al. |
| 8,998,903 B2 | 4/2015 | Price et al. |
| 8,998,904 B2 | 4/2015 | Zeetser et al. |
| 9,011,507 B2 | 4/2015 | Schelling |
| 9,023,052 B2 | 5/2015 | Lietz et al. |
| 9,044,250 B2 | 6/2015 | Olsen et al. |
| 9,060,822 B2 | 6/2015 | Lewis et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| 9,138,244 B2 | 9/2015 | Mebarak et al. |
| D740,424 S | 10/2015 | Dacosta et al. |
| 9,271,769 B2 | 3/2016 | Batsch et al. |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| D766,439 S | 9/2016 | DaCosta |
| 9,452,057 B2 | 9/2016 | Dacosta et al. |
| 9,522,023 B2 | 11/2016 | Haddad et al. |
| 9,592,084 B2 | 3/2017 | Grant |
| 9,642,656 B2 | 5/2017 | Kotuljac et al. |
| 9,668,793 B2 | 6/2017 | Gaudin et al. |
| 9,750,538 B2 | 9/2017 | Soffiatti et al. |
| 9,785,747 B2 | 10/2017 | Geebelen |
| 9,980,760 B2 | 5/2018 | Dacosta et al. |
| 10,028,750 B2 | 7/2018 | Rose |
| 10,064,631 B2 | 9/2018 | Dacosta et al. |
| 10,159,499 B2 | 12/2018 | Dacosta et al. |
| 10,179,013 B2 | 1/2019 | Koay et al. |
| 10,226,287 B2 | 3/2019 | Langford et al. |
| 10,292,713 B2 | 5/2019 | Fallin et al. |
| 10,327,829 B2 | 6/2019 | Dacosta et al. |
| 10,376,268 B2 | 8/2019 | Fallin et al. |
| 10,470,779 B2 | 11/2019 | Fallin et al. |
| 10,856,886 B2 | 12/2020 | Dacosta et al. |
| 10,856,918 B2 | 12/2020 | Dacosta |
| 10,939,939 B1 | 3/2021 | Gil et al. |
| 11,304,705 B2 | 4/2022 | Fallin et al. |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0138669 A1 | 7/2004 | Horn |
| 2004/0172040 A1* | 9/2004 | Heggeness ............ A61B 17/808 606/105 |
| 2005/0004676 A1 | 1/2005 | Schon et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0251147 A1 | 11/2005 | Novak |
| 2005/0267482 A1 | 12/2005 | Hyde |
| 2005/0273112 A1 | 12/2005 | McNamara |
| 2006/0129163 A1 | 6/2006 | McGuire |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0015603 A1 | 1/2008 | Collazo |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2008/0288004 A1 | 11/2008 | Schendel |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0112212 A1 | 4/2009 | Murray et al. |

(56) References Cited

U.S. PATENT DOCUMENTS

| | | |
|---|---|---|
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0210011 A1* | 8/2009 | Den Hartog ....... A61B 17/8014 606/280 |
| 2009/0216089 A1 | 8/2009 | Davidson |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0217332 A1* | 8/2010 | Daniels .............. A61B 17/8061 606/305 |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0009865 A1 | 1/2011 | Orfaly |
| 2011/0093084 A1 | 4/2011 | Morton |
| 2011/0118739 A1 | 5/2011 | Tyber et al. |
| 2011/0178524 A1 | 7/2011 | Lawrence et al. |
| 2011/0245835 A1 | 10/2011 | Dodds et al. |
| 2011/0264149 A1 | 10/2011 | Pappalardo et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 | 5/2012 | Iannotti et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee |
| 2012/0303033 A1 | 11/2012 | Weiner et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0096563 A1 | 4/2013 | Meade et al. |
| 2013/0131821 A1 | 5/2013 | Cachia |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2014/0350561 A1 | 11/2014 | Dacosta et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0015426 A1 | 1/2016 | Dayton |
| 2016/0022315 A1 | 1/2016 | Soffiatti et al. |
| 2016/0135858 A1 | 5/2016 | Dacosta et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0192970 A1* | 7/2016 | Dayton .................. A61B 17/80 606/283 |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0235454 A1* | 8/2016 | Treace ............... A61B 17/8057 |
| 2016/0242791 A1 | 8/2016 | Fallin et al. |
| 2016/0256204 A1 | 9/2016 | Patel et al. |
| 2016/0324532 A1 | 11/2016 | Montoya et al. |
| 2016/0354127 A1 | 12/2016 | Lundquist et al. |
| 2017/0014143 A1 | 1/2017 | Dayton et al. |
| 2017/0014173 A1 | 1/2017 | Smith et al. |
| 2017/0042598 A1 | 2/2017 | Santrock et al. |
| 2017/0042599 A1 | 2/2017 | Bays et al. |
| 2017/0056031 A1 | 3/2017 | Awtrey et al. |
| 2017/0079669 A1 | 3/2017 | Bays et al. |
| 2017/0143511 A1 | 5/2017 | Cachia |
| 2017/0164989 A1 | 6/2017 | Weiner et al. |
| 2017/0209193 A1* | 7/2017 | Hartdegen .......... A61B 17/8004 |
| 2018/0132868 A1 | 5/2018 | Dacosta et al. |
| 2018/0289379 A1 | 10/2018 | Dacosta et al. |
| 2018/0344334 A1 | 12/2018 | Kim et al. |
| 2018/0344371 A1 | 12/2018 | Monk et al. |
| 2019/0046247 A1 | 2/2019 | Gephart |
| 2019/0150994 A1 | 5/2019 | Lewis et al. |
| 2019/0175238 A1* | 6/2019 | Dayton .............. A61B 17/8085 |
| 2019/0357950 A1 | 11/2019 | Bernstein et al. |
| 2020/0015870 A1* | 1/2020 | Treace ............... A61B 17/8635 |
| 2020/0015874 A1 | 1/2020 | Hartson et al. |
| 2020/0229828 A1 | 7/2020 | Wagner et al. |

(56) References Cited

U.S. PATENT DOCUMENTS

| | | | |
|---|---|---|---|
| 2020/0237387 A1 | 7/2020 | Luttrell et al. | |
| 2020/0330109 A1 | 10/2020 | Woodard et al. | |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 103735306 A | 4/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| EP | 3023068 A2 | 5/2016 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 2154143 A | 9/1985 |
| GB | 2154144 A | 9/1985 |
| GB | 2334124 B | 1/2003 |
| IN | 200903719 P1 | 6/2009 |
| IN | 200904479 P2 | 5/2010 |
| IN | 140/DELNP/2012 P1 | 2/2013 |
| IN | 2004/KOLNP/2013 P2 | 11/2013 |
| JP | S635739 A | 1/1988 |
| JP | H0531116 A | 2/1993 |
| JP | 2004174265 A | 6/2004 |
| JP | 2006158972 A | 6/2006 |
| JP | 4134243 B2 | 8/2008 |
| JP | 2008537498 A | 9/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| MD | 756 Z | 11/2014 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015105880 A1 | 7/2015 |
| WO | 2015127515 A2 | 9/2015 |
| WO | 2016134160 A1 | 8/2016 |
| WO | 2020180598 A1 | 9/2020 |

OTHER PUBLICATIONS

Groves, "Operative Report," St. Tammany Parish Hospital, Date of Procedure, Mar. 26, 2014, 2 pages.
D'Amico et al., "Motion of the First Ray: Clarification Through Investigation," Journal of the American Podiatry Association, vol. 69, No. 1, Jan. 1979, pp. 17-23.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Mizuno et al., "Detorsion Osteotomy of the First Metatarsal Bone in Hallux Valgus," Japanese Orthopaedic Association, Tokyo, 1956; 30:813-819.
Eustace et al., "Hallux valgus, first metatarsal pronation and collapse of the medial longitudinal arch—a radiological correlation," Skeletal Radiology, vol. 23, 1994, pp. 191-194.
Collan et al., "The biomechanics of the first metatarsal bone in hallux valgus: A preliminary study utilizing a weight bearing extremity CT," Foot and Ankle Surgery, vol. 19, 2013, pp. 155-161.
Le et al., "Tarsometatarsal Arthrodesis," Operative Techniques in Foot and Ankle Surgery, Section II, Chapter 40, 2011, pp. 281-285.
Coetzee et al., "Revision Hallux Valgus Correction," Operative Techniques in Foot and Ankle Surgery, Section I, Chapter 15, 2011, pp. 84-96.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.

(56) References Cited

OTHER PUBLICATIONS

Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate," Orthopaedics and Traumatology, vol. 7, 1999, pp. 133-143.
Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
DiDomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.
Fallin et al., US Provisional Application Entitled Indexed Tri-Planar Osteotomy Guide and Method, U.S. Appl. No. 62/118,378, filed Feb. 19, 2015, 62 pages.
Fishco, "A Straightforward Guide To The Lapidus Bunionectomy," Podiatry Today, Retrieved online from <https:// www.hmpgloballearningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Gerard et al., "The Modified Lapidus Procedure," Orthopedics, vol. 31, No. 3, Mar. 2008, 7 pages.
Giannoudis et al., "Hallux Valgus Correction," Practical Procedures in Elective Orthopaedic Surgery, Pelvis and Lower Extremity, Chapter 38, 2012, 22 pages.
Greiner, "The Jargon of Pedal Movements," Foot & Ankle International, vol. 28, No. 1, Jan. 2007, pp. 109-125.
Groves, "Functional Position Joint Sectioning: Pre-Load Method for Lapidus Arthrodesis," The Podiatry Institute, Update 2015, Chapter 6, 2015, pp. 23-29.
Hardy et al., "Observations on Hallux Valgus," The Journal of Bone and Joint Surgery, vol. 33B, No. 3, Aug. 1951, pp. 376-391.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Integra, "Integra Large Qwix Positioning and Fixation Screw, Surgical Technique," 2012, 16 pages.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.

Myerson, "Cuneiform-Metatarsal Arthrodesis," The Foot and Ankle, Chapter 9, 1997, pp. 107-117.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Schon et al., "Cuneiform-Metatarsal Arthrodesis for Hallux Valgus, "The Foot and Ankle, Second Edition, Chapter 8, 2002, pp. 99-117.
Sokoloff, "Lapidus Procedure," Textbook of Bunion Surgery, Chapter 15, 1981, pp. 277-287.
Stamatis et al., "Mini Locking Plate as "Medial Buttress" for Oblique Osteotomy for Hallux Valgus," Foot & Ankle International, vol. 31, No. 10, Oct. 2010, pp. 920-922.
Stewart, "Use for BME Speed Nitinol Staple Fixation for the Lapidus Procedure," date unknown, 1 page.
Wukich et al., "Hypermobility of the First Tarsometatarsal Joint," Foot and Ankle Clinics, vol. 10, No. 1, Mar. 2005, pp. 157-166.
Dayton et al., "Biwinged Excision for Round Pedal Lesions," The Journal of Foot and Ankle Surgery, vol. 35, No. 3, 1996, pp. 244-249.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Otsuki et al., "Developing a novel custom cutting guide for curved per-acetabular osteotomy," International Orthopaedics (SICOT), vol. 37, 2013, pp. 1033-1038.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
"Patient to Patient Precision, Accu-Cut, Osteotomy Guide System," BioPro, Foot & Ankle International Journal, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"RAYHACK Ulnar Shortening Generation II Low-Profile Locking System Surgical Technique," Wright Medical Technology, Inc., Dec. 2013, 20 pages.
Rx-Fix Mini Rail External Fixator, Wright Medical Technology, Brochure, Aug. 15, 2014, 2 pages.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.

(56) References Cited

OTHER PUBLICATIONS

Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.
Siddiqui et al. "Fixation Of Metatarsal Fracture With Bone Plate In A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
"Smith & Nephew scores a HAT-TRICK with its entry into the high-growth hammer toe repair market," Smith & Nephew, Jul. 31, 2014, 2 pages.
Stableloc External Fixation System, Acumed, Product Overview, Effective date Sep. 2015, 4 pages.
Stahl et al., "Derotation Of Post-Traumatic Femoral Deformities By Closed Intramedullary Sawing," Injury, vol. 37, No. 2, Feb. 2006, pp. 145-151, (Abstract Only).
Talbot et al.,"Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Tricot et al., "3D-corrective osteotomy using surgical guides for posttraumatic distal humeral deformity," Acta Orthopaedica Belgica, vol. 78, No. 4, 2012, pp. 538-542.
Mtek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fußchirurgie Das V-tek-System," ABW Wissenschaftsverlag GmbH, 2009, 11 pages, including English Abstract.
Weber et al., "A Simple System For Navigation Of Bone Alignment Osteotomies Of The Tibia," International Congress Series, vol. 1268, Jan. 2004, pp. 608-613, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Boffeli et al., "Can We Abandon Saw Wedge Resection in Lapidus Fusion? A Comparative Study of Joint Preparation Techniques Regarding Correction of Deformity, Union Rate, and Preservation of First Ray Length," The Journal of Foot and Ankle Surgery, vol. 58, No. 6, Nov. 2019, published online: Sep. 25, 2019, pp. 1118-1124.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Conti et al., "Effect of the Modified Lapidus Procedure for Hallux Valgus on Foot Width," Foot & Ankle International, Feb. 1, 2020, published online: Oct. 30, 2019, 6 pages.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Hatch et al., "Triplane Hallux Abducto Valgus Classification," The Journal of Foot & Ankle Surgery, vol. 57, No. 5, Sep./Oct. 2018, published online: May 18, 2018, pp. 972-981.
Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.
Li et al., "Evolution of Thinking of the Lapidus Procedure and Fixation," Foot and Ankle Clinics, vol. 25, No. 1, Mar. 2020, published online: Dec. 16, 2019, pp. 18 pages.
Lopez et al., "Metatarsalgia: Assessment Algorithm and Decision Making," Foot and Ankle Clinics, vol. 24, No. 4, Dec. 2019, published online: Sep. 25, 2019, pp. 561-569.
Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.
Walker et al., "The Role of First Ray Insufficiency in the Development of Metatarsalgia," Foot and Ankle Clinics, vol. 24, No. 4, Dec. 2019, published online: Sep. 5, 2019, pp. 641-648.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
"Accu-Cut Osteotomy Guide System," BioPro, Brochure, Oct. 2018, 2 pages.
"Acumed Osteotomiesystem Operationstechnik," Acumed, 2014, 19 pages (including 3 pages English translation).
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Alvine et al., "Peg and Dowel Fusion of the Proximal Interphalangeal Joint," Foot & Ankle, vol. 1, No. 2, 1980, pp. 90-94.
Anderson et al., "Uncemented STAR Total Ankle Prostheses," The Journal of Bone and Joint Surgery, vol. 86(1, Suppl 2), Sep. 2004, pp. 103-111, (Abstract Only).

(56) References Cited

OTHER PUBLICATIONS

Bednarz et al., "Modified Lapidus Procedure for the Treatment of Hypermobile Hallux Valgus," Foot & Ankle International, vol. 21, No. 10, Oct. 2000, pp. 816-821.
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International, vol. 32, No. 5, May 2011, pp. 567-569.
Carr et al., "Correctional Osteotomy for Metatarsus Primus Varus and Hallux Valgus," The Journal of Bone and Joint Surgery, vol. 50-A, No. 7, Oct. 1968, pp. 1353-1367.
Coetzee et al., "The Lapidus Procedure: A Prospective Cohort Outcome Study," Foot & Ankle International, vol. 25, No. 8, Aug. 2004, pp. 526-531.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.
Dayton et al., "Relationship Of Frontal Plane Rotation Of First Metatarsal To Proximal Articular Set Angle And Hallux Alignment In Patients Undergoing Tarsometatarsal Arthrodesis For Hallux Abducto Valgus: A Case Series And Critical Review Of The Literature," The Journal of Foot and Ankle Surgery, vol. 52, No. 3, May/Jun. 2013, pp. 348-354.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
EBI Extra Small Rail Fixator, Biomet Trauma, retrieved Dec. 19, 2014, from the Internet: < http://footandanklefixation.com/product/biomet-trauma-ebi-extra-small-rail-fixator>, 7 pages.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
"Futura Forefoot Implant Arthroplasty Products," Tornier, Inc., 2008, 14 pages.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.
Garthwait, "Accu-Cut System Facilitates Enhanced Precision," Podiatry Today, vol. 18, No. 6, Jun. 2005, 6 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

Gotte, "Entwicklung eines Assistenzrobotersystems für die Knieendoprothetik," Forschungsberichte, Technische Universitat Munchen, 165, 2002, 11 pages, including partial English Translation.
Gregg et al., "Plantar plate repair and Weil osteotomy for metatarsophalangeal joint instability," Foot and Ankle Surgery, vol. 13, 2007, pp. 116-121.
Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
"HAT-TRICK Lesser Toe Repair System," Smith & Nephew, Brochure, Aug. 2014, 12 pages.
"HAT-TRICK Lesser Toe Repair System, Foot and Ankle Technique Guide, Metatarsal Shortening Osteotomy Surgical Technique," Smith & Nephew, 2014, 16 pages.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Mortier et al., "Axial Rotation of the First Metatarsal Head in a Normal Population and Hallux Valgus Patients," Orthopaedics and Traumatology: Surgery and Research, vol. 98, 2012, pp. 677-683.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
"Lag Screw Target Bow," Stryker Leibinger GmbH & Co. KG, Germany 2004, 8 pages.
Lapidus, "The Author's Bunion Operation From 1931 to 1959," Clinical Orthopaedics, vol. 16, 1960, pp. 119-135.
Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Magin, "Computernavigierter Gelenkersatz am Knie mit dem Orthopilot," Operative Orthopädie und Traumatologie, vol. 22, No. 1, 2010, pp. 63-80, including English Abstract on p. 64.
Magin, "Die belastungsstabile Lapidus-Arthrodese bei Hallux-valgus-Deformität mittels IVP-Plattenfixateur (V-TEK-System)," Operative Orthopädie und Traumatologie, vol. 26, No. 2, 2014, pp. 184-195, including English Abstract on p. 186.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and

(56) References Cited

OTHER PUBLICATIONS

Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).
International Patent Application No. PCT/US2020/045393, International Search Report and Written Opinion mailed Nov. 20, 2020, 10 pages.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Wienke et al., "Bone Stimulation For Nonunions: What the Evidence Reveals," Podiatry Today, vol. 24, No. 9, Sep. 2011, pp. 52-57.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Dayton et al., "A User-Friendly Method of Pin Site Management for External Fixators," Foot and Ankle Specialist, Sep. 16, 2011, 4 pages.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "Clarification of the Anatomic Definition of the Bunion Deformity," The Journal of Foot and Ankle Surgery, vol. 53, 2014, pp. 160-163.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Catanese et al., "Measuring Sesamoid Position in Hallux Valgus: When Is the Sesamoid Axial View Necessary," Foot and Ankle Specialist, 2014, 3 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Complications of Metatarsal Suture Techniques for Bunion Correction: A Systematic Review of the Literature," The Journal of Foot and Ankle Surgery, Article in Press, 2015, 3 pages.
DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Diseas of the First Metatarsalphalangeal Joint," Podiatry Management, Jan. 2013, pp. 137-142.
DeCarbo et al., "Locking Plates: Do They Prevent Complications?," Podiatry Today, Apr. 2014, 7 pages.
Easley et al., "Current Concepts Review: Hallux Valgus Part II: Operative Treatment," Foot and Ankle International, vol. 28, No. 6, Jun. 2007, pp. 748-758.
KIM et lal., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Easley et al., "What is the Best Treatment for Hallux Valgus?," Evidence-Based Orthopaedics—The Best Answers to Clinical Questions, Chapter 73, 2009, pp. 479-491.
Shurnas et al., "Proximal Metatarsal Opening Wedge Osteotomy," Operative Techniques in Foot and Ankle Surgery, Section I, Chapter 13, 2011, pp. 73-78.
Defendant Fusion Orthopedics LLC's Invalidity Contentions, No. CV-22-00490-PHX-SRB, US District Court for the District of Arizona, Aug. 27, 2022, 41 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics

(56) References Cited

OTHER PUBLICATIONS

LLC's Invalidity Contentions, No. CV-22-00490-PHX-SRB, US District Court for the District of Arizona, Aug. 27, 2022, 151 pages.
Calafi, "Basic Principles and Techniques of Internal Fixation of Fractures," Mar. 2014, 57 pages.
"Locking versus nonlocking plates—Advantages to a locking plate/screw system," AO Surgery Reference, retrieved online from <https://surgeryreference.aofoundation.org/cmf/basic-technique/locking-plate-principles> and believed to be publicly available prior to Jan. 18, 2021, 14 pages.
Grawe et al., "Fracture fixation with two locking screws versus three non-locking screws," Bone Joint Res, vol. 1, No. 6, Jun. 2012, pp. 118-124.
Cronier et al., "The concept of locking plates," Orthopaedics & Traumatology: Surgery & Research, vol. 96, No. 4, Supplement, Jun. 2010, pp. S17-S36.
"Screw Basics 101—The Differences Between Orthopedic Screws," retrieved online from <https://mdrao.ca/wp-content/uploads/2018/05/SCREW-BASICS-101.pdf> and believed to be publicly available prior to Jan. 18, 2021, 11 pages.
"Screw thread," Wikipedia.com, retrieved online from <https://en.wikipedia.org/wiki/Screw_thread>, last edited Jun. 3, 2023, and believed to be publicly available prior to Jan. 18, 2021, 15 pages.
International Patent Application No. PCT/US2022/012668, International Search Report and Written Opinion mailed Apr. 11, 2022, 14 pages.

\* cited by examiner

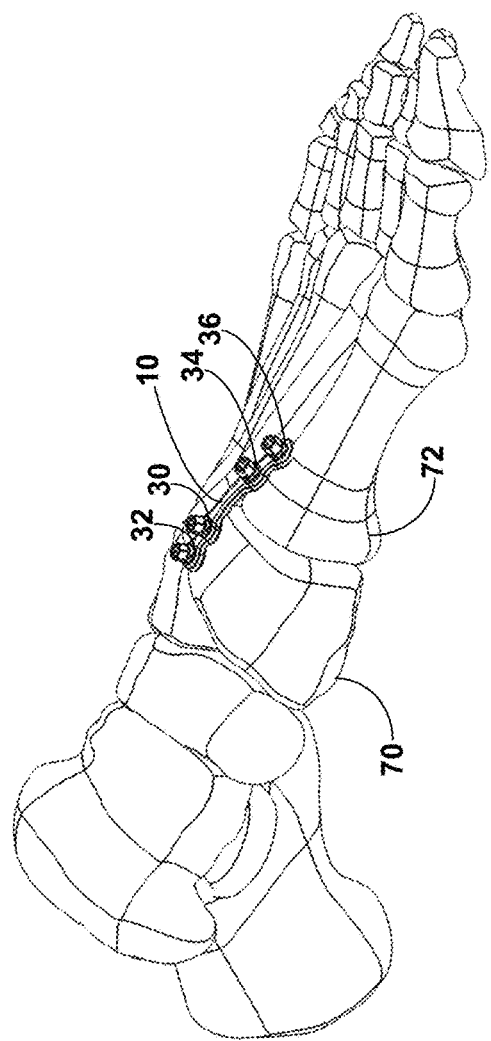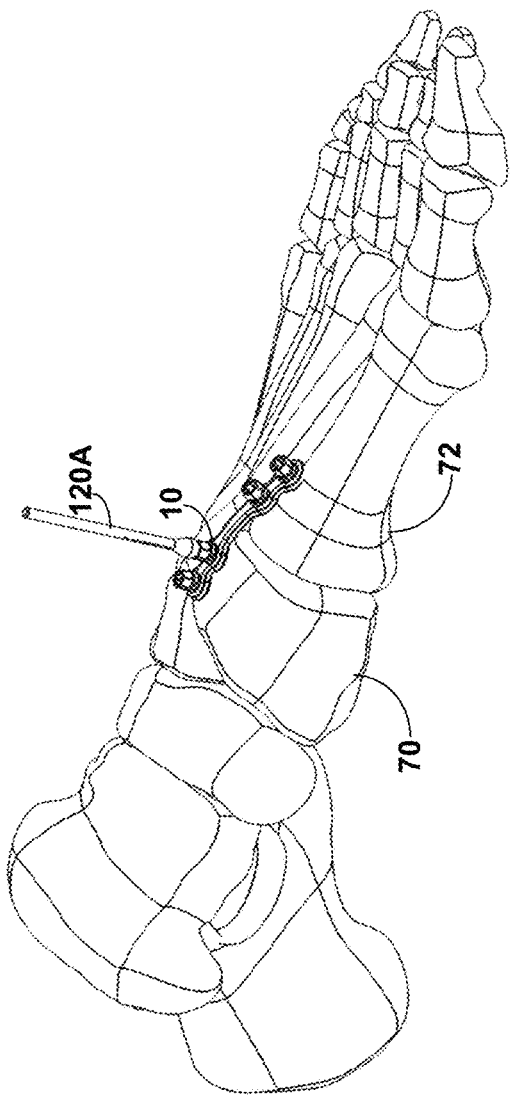
FIG. 10
FIG. 11

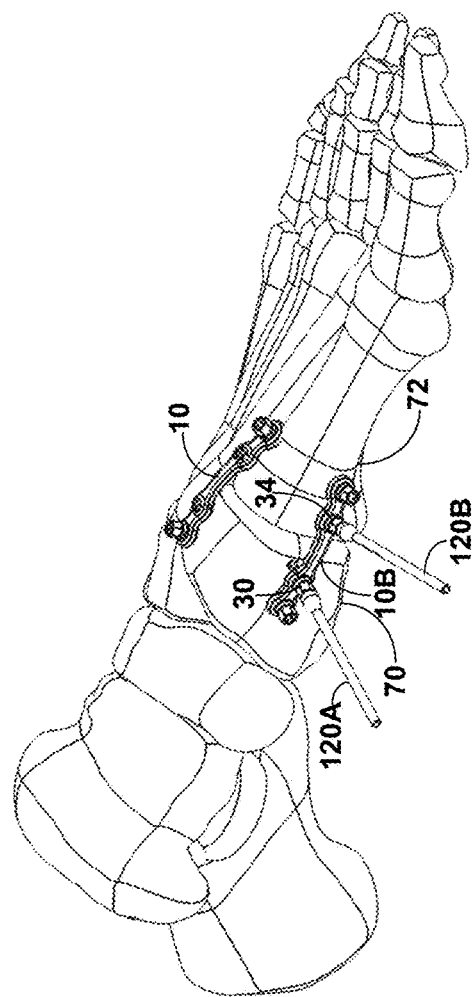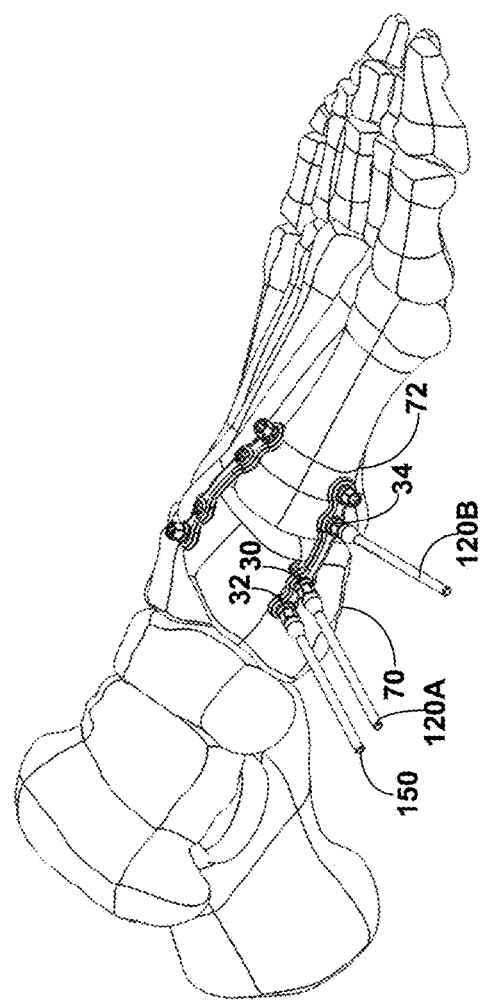

CONTOURED BONE PLATE WITH LOCKING SCREW FOR BONE COMPRESSION, PARTICULARLY ACROSS A TARSOMETATARSAL JOINT

RELATED MATTERS

This application claims the benefit of U.S. Provisional Patent Application No. 63/138,726, filed Jan. 18, 2021, the entire contents of which are incorporated herein by reference.

TECHNICAL FIELD

This disclosure relates to bone plates and methods for fixating bones using a bone plate, including compressing opposed bone ends together using a bone plate.

BACKGROUND

Bones, such as the bones of a foot, may be anatomically misaligned. In certain circumstances, surgical intervention is required to correctly align the bones to reduce patient discomfort and improve patient quality of life. Surgical intervention may involve cutting one or more of the misaligned bones and then physically realigning the bones into an anatomically corrected position. A bone plate or multiple bone plates may be used to hold the bones in the anatomically corrected position, helping to prevent the bones from shifting back to their misaligned position.

SUMMARY

In general, this disclosure is directed to bone plates and screws, systems incorporating bone plates and screws, and methods of using bone plates. In some examples, bone plate systems and techniques are described to facilitate compression (e.g., angular compression) between opposed ends of two bone portions to which a bone plate is attached, which may be different portions of the same bone or two different bones separated by a joint. The force generated by the plating system may be asymmetrically distributed across the faces of the bone ends being pressed together, e.g., such that there is a greater force on a side of the bone ends opposite the plate than on a side of the bone ends closer to the plate. This may help facilitate angular correction of the bone portions relative to each other and/or promote healing (e.g., fusion) between the bone portions in a corrective orientation.

In some implementations, a bone plate includes an elongated body having a length greater than a maximum width and thickness. For example, the bone plate may have a length sized to span a tarsometatarsal joint separating a metatarsal from an opposed cuneiform. The bone plate may include a bend that displaces a portion of the bone plate positionable over the joint between the two bone portions away from the joint. As a result, the bone plate may include a first end contacting one bone portion and a second end contacting the second bone portion, with an intermediate portion between the two ends displaced off of one or both bone portions and/or the joint between the two bone portions.

To secure the bone plate to the bone portions, the bone plate can include multiple fixation holes extending through the bone plate, including at least one fixation hole positionable over the first bone portion and at least one additional fixation hole positionable over the second bone portion. One or more of these fixation holes may include threading partially or fully encircling the fixation hole to facilitate engagement with threading on the head of a locking screw insertable through the fixation hole and into an underlying bone.

To both secure the locking plate to an underlying bone portion and achieve compression between the ends of the two bone portions being secured together with the bone plate according to some examples, at least one locking screw may be used that is configured to both interlock with the bone plate and deform the bone plate when driven beyond its initially engaged position in the bone plate. For example, as an arch in the bone plate is physically deformed toward a flattened or unbent profile (e.g., resulting in a residual arch of smaller height after deformation), an underside of the plate may be placed in tension and a topside of the plate placed in compression. As a result, a moment force may be applied that has an asymmetrically distributed magnitude across the end faces of the bones being compressed. When used, the locking screw may be configured to interlock with the bone plate and deform the bone plate by controlling the compression ratio of the locking screw. The compression ratio of the bone screw may be controlled by adjusting the pitch of the threading on the head of the screw relative to the pitch of the threading on the shaft of the screw and/or by controlling the lead of the head relative to the lead of the shaft.

Traditional bone plate systems utilize one of two different types of screws: compression screws or locking screws. Compression screws are screws that have a threaded shaft but do not have a threaded head. In use, a compression screw can be driven until the head of the screw contacts the bone plate and then further driven into the bone to compress the bone plate. By contrast, locking screws have both a threaded head and a threaded shaft. However, locking screws are generally designed to be screwed until the threaded head is interlocked with the counter threading on the bone plate without causing any compression on the bone plate.

In accordance with some examples of the present disclosure, a bone plate is provided with one or more locking screws that achieve both interlocking between the head of the screw and the counter threading around the fixation hole on the bone plate as well compression of the bone plate during rotation. The pitch of the threading on the shaft of the screw may be sufficiently greater than the pitch of the threading on the head of the screw to achieve both interlocking and compression. Additionally or alternatively, the lead of the threading on the shaft may be greater than the lead of the threading on the head to generate a compressive force as the locking screw is inserting into an underlying bone. In either case, as the threading on the head of the screw rotationally interlocks with the counter threading around the fixation hole, the threading on the shaft may continue to draw the bone plate engaged with the threading on the head down toward the bone. As a result, a bend in the bone plate may deform (e.g., elastically and/or plastically) toward the bone portions being fixated.

In some examples, the bone plate is provided with the one or more locking screws configured for both interlocking with the bone plate and for compression. The bone plate has a bend portion. The bend portion may be a region of the bone plate between opposed ends of the bone plate that is non-planar with one or both end portions (e.g., prior to deformation and/or installation). The bend portion may be offset from the end portions in one or more planes. For example, when one end of the bone plate is positioned in contact with one bone portion and the second end of the bone plate is positioned in contact with the other bone portion, the bend portion may define a gap between a bone-facing surface of the bone plate in the bend portion and the surfaces of the underlying bone(s). This gap may be reduced or eliminated through flattening of the bend upon installation of the one or more locking screws that are also configured to achieve compression.

With the bend portion of the bone plate positioned over the joint between the two bone portions to be fixated together, one or more locking screws configured for compression may be installed through corresponding fixation holes in the bone plate and into underlying bone. As the one or more locking screws are installed, the bend portion in the bone plate may deform toward the joint between the two bone portions. With the bone plate deformed from an initial bend to a reduced bend profile, the bone plate may function as a spring providing a distributed load through the end faces of the bones being pressed together, e.g., with a greater force on the cortex of the bones on an opposite the plate than the force on the cortex of the bones closest to the plate. As a result, the force provided by the tensioned bone plate may be angular, e.g., helping to reinforce a bone realignment performed prior to fixation using the bone plate.

In some examples, a bone plate with a bend portion may be positioned over a joint between two adjacent bone portions to be fixated and one or more locking screws configured for compression installed through the fixation holes of the bone plate into the underlying bone portions. One or more additional screws (e.g., compression screws, locking screws not configured for compression) may also be installed through one or more fixation holes of the bone plate into one or more underlying bone portions.

Additionally or alternatively, one or more driving pins may be used to help install and pre-compress the bone plate prior to installation of the screws. When used, a driving pin may include a threaded head, a shaft, and an enlarged region having a cross-sectional area larger than a cross-sectional area of the fixation hole through which the head of driving pin is to be inserted. One or more driving pins can be installed through the fixation holes of the bone plate into the underlying bone portions, e.g., by screwing the distal head of the one or more driving pins into the underlying bone portions. As the driving pin(s) are driven deeper into the underlying bone portion(s), the enlarged region of the driving pin can press against a top surface of the bone plate adjacent a corresponding fixation hole. This can cause the bone plate to compress toward the bone portions being fixated. One or more individual driving pins can then be removed and corresponding screws installed to complete the installation process.

In yet additional examples, a bone plate with a bend portion may be pre-deformed (e.g., pre-compressed) before or concurrent with being positioned over a joint between two adjacent bone portions to be fixated (and prior to installation of any screws or, optionally, driving pins). For example, using hand manipulation and/or a bending instrument, the bend portion of the plate may be compressed toward a more planar shape and held in compression while placed spanning the joint between the bone portions being fixated. The bone screws and/or driving pins can then be installed through the fixation holes of the bone plate while held in compression. One example bending instrument that may be used is a pair of plate bending arms inserted through fixation holes on opposite sides of the apex of the bend portion (e.g., into drill guides installed in the fixation holes), which are then used to manipulate the bone plate.

In one example, a method of applying a bone plate across a tarsometatarsal joint is described. The method includes positioning a bone plate across a tarsometatarsal joint separating a metatarsal from a cuneiform. The bone plate has a first fixation hole, a second fixation hole, and a bend between the first fixation hole and the second fixation hole. Positioning the bone plate across the tarsometatarsal joint involves positioning the bend over the tarsometatarsal joint with a gap between a bone-facing surface of the bone plate and the tarsometatarsal joint. The method also involves inserting a locking screw through the first fixation hole. The locking screw has a head with a head thread and a shaft with a shaft thread. The shaft thread has a pitch greater than a pitch of the head thread, and the first fixation hole includes threading for engaging with the head thread. The method involves screwing the locking screw into a metatarsal or a cuneiform under the first fixation hole until the head thread of the locking screw is engaged with the threading defined by the first fixation hole and further screwing the locking screw into the metatarsal or the cuneiform, thereby deforming the bend in the bone plate toward the tarsometatarsal joint.

In another example, an orthopedic fixation system is described. The system includes a bone plate having a length defining a longitudinal axis extending from a proximal end of the body to a distal end of the body. The bone plate has a top surface and a bone-facing surface opposite the top surface and includes a first fixation hole extending through the body and a second fixation hole extending through the body. The length of the bone plate is sized to cross a tarsometatarsal joint with one of the first fixation hole and the second fixation hole positioned over a metatarsal and an other of the first fixation hole and the second fixation hole positioned of a cuneiform. At least the first fixation hole includes threading, and the bone plate includes a bend offsetting a portion of the bone plate between the first fixation hole and the second fixation hole relative portions of the bone plate defining the first fixation hole and the second fixation hole. The system also includes a locking screw having a head with a head thread and a shaft with a shaft thread, the shaft thread having a pitch greater than a pitch of the head thread. The locking screw exhibits a compression ratio defined by the pitch of the shaft thread divided by the pitch of the head thread. The locking screw is configured to be inserted through the first fixation hole into at least one of the metatarsal and the cuneiform and the head thread engaged with the threading defined by the first fixation hole. The compression ratio is effective to cause the bone plate to deform when the head thread is fully engaged with the threading defined by the first fixation hole and the screw is further turned.

In another example, a method is described that includes tensioning a bone plate having a first fixation hole, a second fixation hole, and a bend between the first fixation hole and the second fixation hole by bending the bone plate against the bend toward a flattened profile, thereby providing a tensioned bone plate. The method includes positioning the tensioned bone plate across a tarsometatarsal joint separating a metatarsal from a cuneiform and inserting a locking screw through the first fixation hole. The locking screw has a head with a head thread and a shaft with a shaft thread. The shaft thread having a pitch greater than a pitch of the head thread, and the first fixation hole includes threading for engaging with the head thread. The method also includes screwing the locking screw into the metatarsal or the cuneiform under the first fixation hole until the head thread of the locking screw is engaged with the threading defined by the first fixation hole.

The details of one or more examples are set forth in the accompanying drawings and the description below. Other features, objects, and advantages will be apparent from the description and drawings, and from the claims.

BRIEF DESCRIPTION OF DRAWINGS

FIGS. 10-15 illustrate example procedure steps for attaching a bone plate to a medial cuneiform and a first metatarsal separated by tarsometatarsal joint.

FIGS. 16-22 illustrate example procedural steps that may be performed after the procedure steps described with respect to FIGS. 10-15.

DETAILED DESCRIPTION

The present disclosure is generally directed to bone plates, systems and kits that include one or multiple bone plates and screws, and method of using one or multiple bone plates and corresponding screws. In an exemplary application, a bone plate and screw system according to the disclosure can be useful for internal fixation of a bone or bones during a surgical procedure, such as a bone alignment, osteotomy, fusion procedure, fracture repair, and/or other procedures where one or more bones are to be set in a desired position. Such a procedure can be performed, for example, on bones (e.g., adjacent bones separated by a joint or different portions of a single bone) in the foot or hand, where bones are relatively small compared to bones in other parts of the human anatomy. In one example, a procedure utilizing an embodiment of the bone plate and screw system can be performed to correct an alignment between a metatarsal (e.g. a first metatarsal) and a cuneiform (e.g., a medial cuneiform), such as a bunion correction. An example of such a procedure is a lapidus procedure. In another example, the procedure can be performed by modifying an alignment of a metatarsal (e.g. a first metatarsal). An example of such a procedure is a basilar metatarsal osteotomy procedure.

Example screw configurations and methods of installing bone plate and screw systems according to the disclosure will be described in greater detail with respect to FIGS. 3-24. However, an example bone plate that may be used in accordance with the disclosure will first be described with respect to FIGS. 1 and 2.

Figure 1:
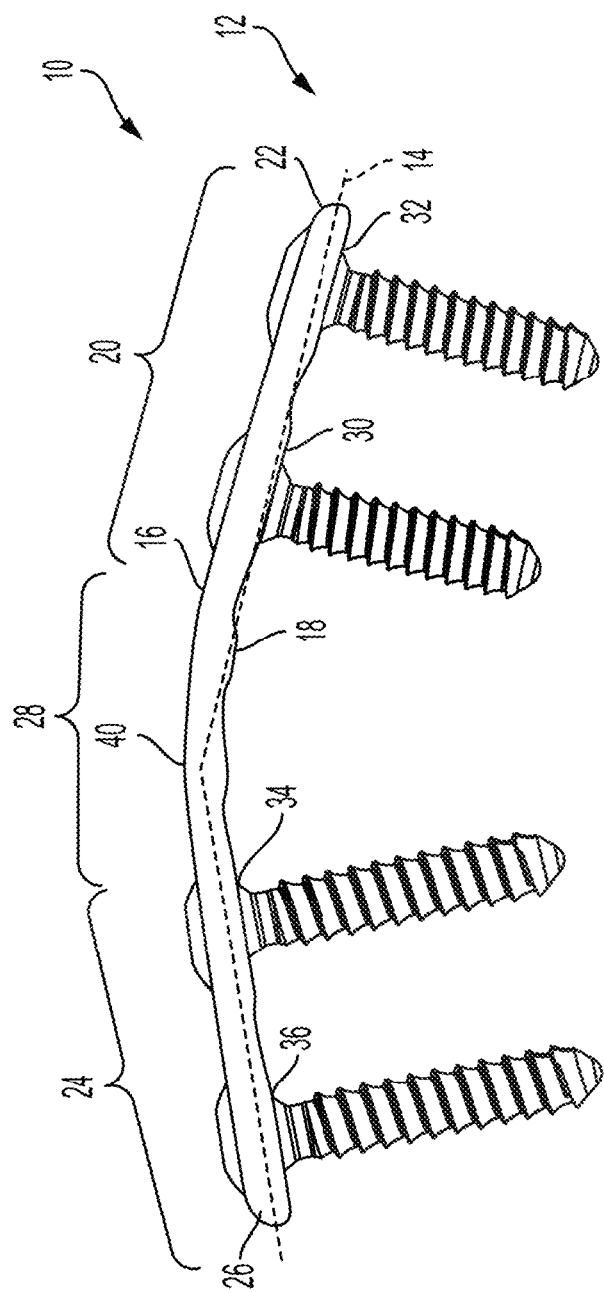
FIGS. 1 and 2 are side and top views, respectively, of an example bone plate that may be used to achieve both fixation and compression across two bone portions.
Figure 2:
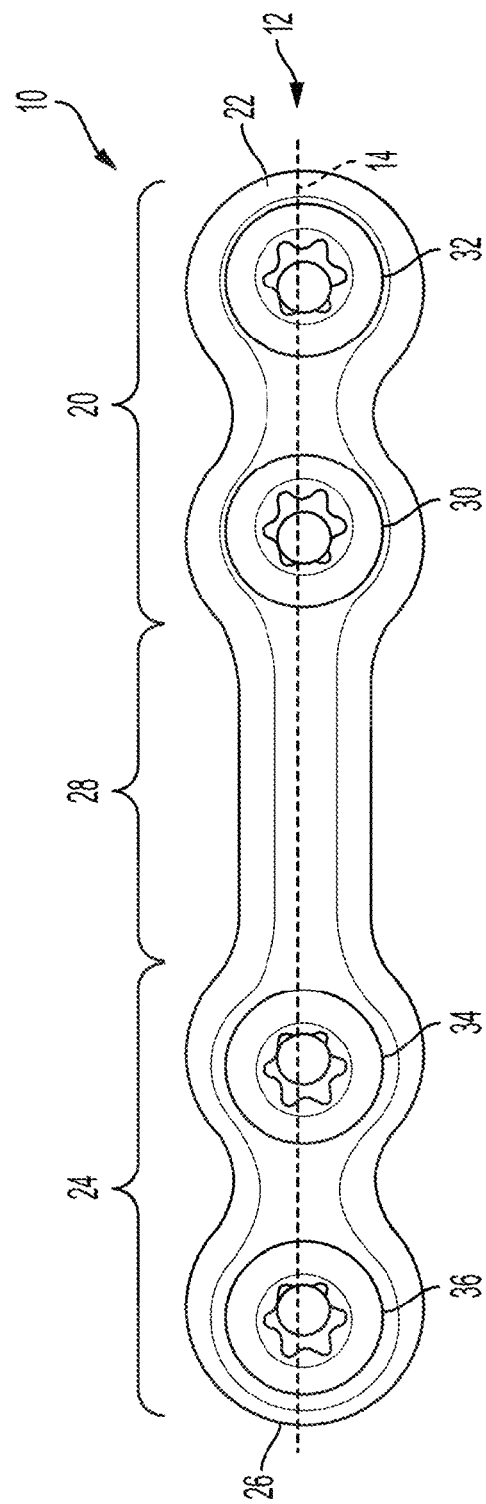

FIGS. 1 and 2 are side and top views, respectively, of an example bone plate 10 that may be used to achieve both fixation and compression across two bone portions. Bone plate 10 defines a body 12 having a central longitudinal axis 14. The body of the bone plate 10 has a top surface 16 and a bone facing surface 18, where the bone facing surface 18 is on a side of the body 12 opposite the top surface 16. In some implementations, bone plate 10 is positioned so that the bone facing surface 18 interfaces with and/or is in contact with one or both bone portions along at least a portion of the length of longitudinal axis 14. For convenience, "bone facing surface" will refer to the side of the bone plate generally facing bone when the plate is positioned on one or more bones, regardless of whether there is more than one surface contacting the bone when bone plate 10 is applied.

Body 12 of bone plate 10 can define a distal region 20 at or near a first terminal end 22 and a proximal region 24 at or near a second terminal end 26 that is opposite the first terminal end of the body. The distal region 20 may be separated from the proximal region 24 by an intermediate region 28. For example, bone plate 10 may include one or more fixation holes extending through the thickness of body 12. In these examples, body 12 may include one or more fixation holes in distal region 20, one or more additional fixation holes in proximal region 24, and an intermediate region 28 devoid of fixation holes positioned between the distal region 20 and the proximal region 24.

In the illustrated example of FIGS. 1 and 2, distal region 20 of bone plate 10 has at least one fixation hole, which is illustrated as two fixation holes 30 and 32. Proximal region 24 also has at least one fixation hole, which is also illustrated as two fixation holes 34 and 36. First fixation hole 30 extending through body 12 in distal region 20 is the fixation hole closest to the intermediate region 28 on the distal side of the bone plate which, as will be described, can include a bend offsetting the intermediate region from an underlying bone surface. Second fixation hole 34 extending through body 12 in proximal region 24 is the fixation hole is the fixation hole closest to the intermediate region 28 on the proximal side of the bone plate. Third fixation hole 32 in the illustrated example is located between first fixation hole 30 and the first terminal end 22 of the bone plate. Fourth fixation hole 36 in the example is located between second fixation hole 34 and the second terminal end 26 of the bone plate.

Each feature described as a fixation hole may be an opening extending through the thickness of body 12 that is sized to receive a corresponding screw. Each fixation hole may typically have a circular cross-sectional shape although may have other cross-sectional shapes without departing from the scope of the disclosure. The fixation hole may extend perpendicularly through the thickness of body 12 or may taper (e.g., such that the hole is larger adjacent top surface 16 than adjacent bone-facing surface 18). In still other examples, the fixation hole may extend at a non-perpendicular angle through the thickness of body 12 and/or be configured for polyaxial screw alignment.

Although bone plate 10 is illustrated as being configured with four fixation holes 30, 32, 34, and 36, the bone plate may include fewer fixation holes or more fixation holes. For example, distal region 20 and proximal region 24 of bone plate 10 may each include fewer fixation holes (e.g., one) and/or more fixation holes (e.g., three, four). The dimensions (e.g., length) of the distal and proximal regions 20, 24 can be adjusted to accommodate the particular number of fixation holes included. Further, while the fixation holes on bone plate 10 are illustrated as being co-axial with each other along the longitudinal axis 14 of the bone plate, the bone plate may include one or more branches each containing a fixation hole extend off of the longitudinal axis. As a result, the one or more fixation holes in these branch(es) may be non-co-linear with the remaining co-axially arranged fixation holes. For instance, in various examples, bone plate 10 may include at least one branch extending outwardly from the longitudinal axis 14 of the bone plate to define at least one of a Y-shape, an L-shape, a T-shape, a U-shape, and/or other shape profile.

Bone plate 10 may include a bend 40. Bend 40 may be a portion of bone plate 10 that is out of plane with one or more planes in which first fixation hole 30 and second fixation hole 34 are positioned. In some examples, first terminal end 22 and second terminal end 26 of bone plate 10 are coplanar (e.g., such that the terminal ends of the bone plate can be positioned in the same plane). Bend 40 may offset at least a portion of bone plate 10 out of the plane in which first terminal end 22 and second terminal end 26 are positioned.

As will be described, when bone plate 10 containing bend 40 is positioned across a joint between two bone portions, at least part of distal region 20 (e.g., including first terminal end 22) may contact one bone portion and at least part of proximal region 24 (e.g., including second terminal end 26) may contact the other bone portion. Bend 40 may elevate a portion of bone plate 10 off the surface of one or both bone portions across the joint. As a result, a gap may exist between bone-facing surface 18 of bone plate 10 in the region of the bend and the underlying bone portions. The size of this gap may be reduced (optionally without eliminating the gap) upon insertion of one or more screws and/or compression of the bone plate.

Bend 40 of bone plate 10 may curve distal region 20 toward proximal region 24 about intermediate region 28. For example, bend 40 can reduce the distance between first terminal end 22 and second terminal end 26 as compared to when body 12 is flat or planar. Bend 40 can be defined by a sharp transition (e.g., V-shape) or a radius of curvature. The radius of bend 40 can vary or be constant as a function of longitudinal position on body 12, and/or be concentrated in one or more portions of the body, such as the portion of the body between the proximal and distal regions 20, 24. In some examples, bend 40 is defined by a radius of curvature ranging from approximately 10° to approximately 45°, such as from approximately 15° to approximately 35°. In other examples, bend 40 may be defined by a radius of curvature ranges from 45° to 135°, such as from approximately 75° to approximately 105°. Other angles of bend are also possible.

When bone plate 10 is configured with a bend, the entire length of the bone plate may be bent (e.g., to define a radius of curvature) or only one region of the bone plate may be bent out of plane relative to a remainder of the bone plate. Therefore, when discussing that bone plate 10 may have a bend 40 in the intermediate region 28 between proximal and distal regions 20, 24, it should be appreciated that the bend may or may not be isolated to that region. Rather, bend 40 may define an apex in intermediate region 28 between first fixation hole 30 and second fixation hole 34, e.g., such that the peak of the bone plate and/or maximum offset relative to the first and second fixation holes (and/or first and second terminal ends) is within this region. Depending on the application, the apex of bend 40 may be positioned along the length of bone plate 10 such that, when the bone plate is positioned across a joint separating to bone portions, the apex is substantially centered over the joint (e.g., within plus or minus 3 mm of the joint, such as plus or minus 2 mm of the joint, or plus or minus 1 mm of the joint).

Bone plate 10 can be formed of any suitable biocompatible material or combinations of materials, such as stainless steel, nitinol, titanium, and/or polymeric materials (e.g., polyether ether ketone or PEEK). Bend 40 can be formed by manufacturing bone plate 10 to include the bend (e.g., by casting or machining the bone plate initiate that includes bend 40). Alternatively, bone plate 10 can be fabricated as a planar plate that is subsequently bent (e.g., plastically deformed) to create bend 40.

Bone plate 10 can have a variety of features and configurations. For example, the width of bone plate 10 may be constant across the length of the bone plate or may vary such that one or more regions of the bone plate have a width greater than one or more other regions of the bone plate. For instance, in some implementations, bone plate 10 may have a larger width in regions containing fixation holes and a narrow width in regions between adjacent fixation holes. Additionally or alternatively, the thickness of bone plate 10 may be constant across the length of the bone plate or may vary such that one or more regions of the bone plate have a thickness greater than one or more other regions of the bone plate. For example, bone plate 10 may include pads projecting down from a remainder of the bone-facing surface 18 (e.g., in the region of the fixation holes) and/or channels that are recessed relative to a remainder of the bone-facing surface to define different thicknesses across the length of the bone plate. Example bone plate features that may be used are described in U.S. Pat. No. 10,245,088, titled "Bone Plating System and Method," the entire contents of which are incorporated herein by reference.

Bone fasteners can be used to secure bone plate 10 to underlying bone portions. As briefly discussed above, at least one of the bone fasteners used to secure the bone plate to an underlying bone portion may be structured as a locking screw that is configured to both interlock with the bone plate and achieve compression, thereby deforming bend 40 toward underlying bone surfaces.

Figure 3:
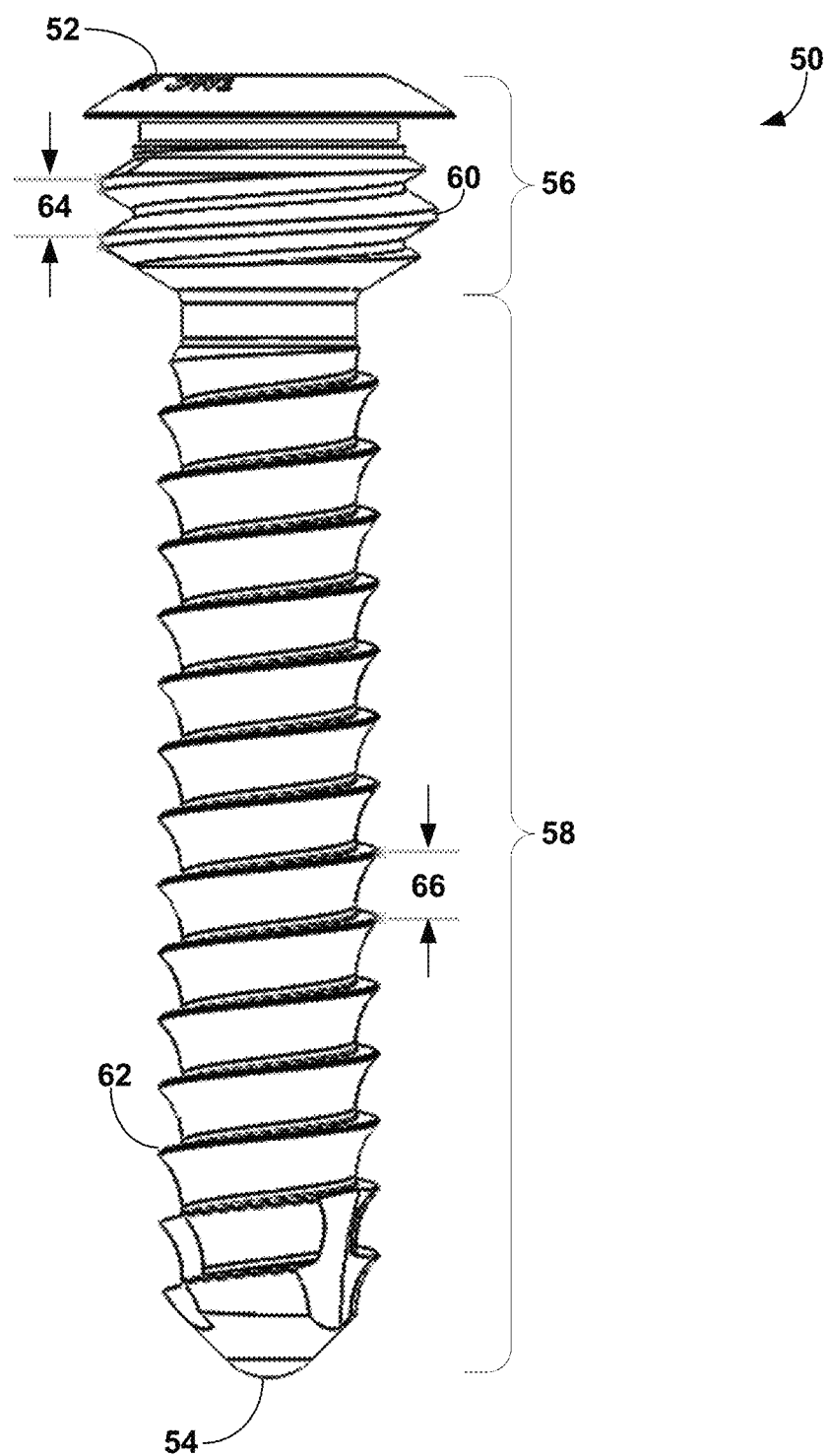
FIG. 3 is side view of an example locking screw that can be used with the bone plate of FIGS. 1 and 2.

FIG. 3 is side view of an example locking screw 50 that can be used with bone plate 10 of FIGS. 1 and 2. Locking screw 50 extends from a proximal end 52 to a distal end 54. Locking screw 50 includes a head 56 and a shaft 58. Head 56 of locking screw 50 includes thread 60 partially or fully encircling the head for engaging with counter threading encircling a fixation hole of bone plate 10 into which the locking screw is intended to be inserted. Thread 60 may be referred to as head thread for purposes of discussion. Shaft 58 of locking screw 50 includes thread 62 partially or fully encircling the shaft for engaging with a bone portion underlying a fixation hole of bone plate 10 through which locking screw 50 is inserted. Thread 62 may be referred to as shaft thread for purposes of discussion.

Thread 60 and 62 may each be a helical structure used to convert rotational motion into linear movement or force. Thread 60 and 62 may be defined by a ridge of material wrapped around an inner cylinder or cone of material in the form of a helix, to define a straight thread or a tapered thread, respectively.

Locking screw 50 can be characterized by both its lead and its pitch. Lead is the distance along the axis of the screw that is covered by one complete rotation of the screw (360°). Pitch is the distance from the crest of one thread to the next. In some examples, locking screw 50 is configured as a single lead screw, e.g., such that there is only one threaded ridge wrapped around the body of the screw. When so configured, each time the body of the screw is rotated one turn (360°), it has advanced axially by a distance equal to the pitch or spacing between adjacent ridges along the axis of the screw. In other examples, locking screw 50 is configured as a multi-lead screw, such as a dual lead screw, a tri-lead screw, or a quad-lead screw, such that each time the body of the screw is rotated one turn, it is advanced axially by a multiple of the pitch or spacing between adjacent ridges. In other words, the pitch and lead may be equal for a single lead screw but the lead may be the pitch or spacing between adjacent ridges multiplied by the number of screw starts for a multi-lead screw (e.g., pitch×2 for a dual-lead screw, pitch×3 for a tri-lead screw).

In accordance with some implementations of the present disclosure, locking screw 50 is configured to be inserted through a fixation hole of bone plate 10 and driven into an underlying bone portion. The locking screw can be configured with a compression ratio greater than 1.0. As used herein, the term "compression ratio" means the pitch of the shaft thread multiplied by the number of number of starts on the shaft thread with that sum being divided by the pitch of head thread multiplied by the starts on the head thread. This can be represented by the following equation:

$$\text{Compression Ratio} = \frac{\text{Pitch of Shaft Thread} \times \text{Number of Shaft Thread Starts}}{\text{Pitch of Shaft Thread} \times \text{Number of Head Thread Starts}}$$

In practice, the head thread 60 may typically be a single start threading. In such configurations, the compression ratio may be the pitch of shaft thread 62 divided by the pitch of head thread 60 when shaft thread 62 defines a single start screw. When shaft thread 62 defines a dual-start screw, the compression ratio may be twice the pitch of shaft thread 62 divided by the pitch of head thread 60.

The differential pitch and/or starts between head thread 60 and shaft thread 62 may be selected to be effective to deliver a compressive force to bone plate 10 when locking screw 50 is inserted into the bone plate. For example, when bone plate 10 is secured to one bone portion with a bone fastener, locking screw 50 may be inserted through a fixation hole across a joint into another bone portion. As head thread 60 of locking screw 50 engages with counter threading encircling the fixation hole of the bone plate into which the screw is inserted, shaft thread 62 may continue drawing the screw down into the underlying bone. As a result, bend 40 in bone plate 10 may deform by bowing toward the bone portions. As locking screw 50 continues to be screwed into the fixation hole a bone plate 10, bend 40 may further deform. Locking screw 50 may be inserted into the underlying bone until head 56 is fully seated within a receiving opening defined by the fixation hole the bone plate.

The specific compression ratio that is effective to achieve compression of bone plate 10 during use may vary, e.g., based on the thickness of the plate. In general, compression ratio may be greater than 1.0. As a result, one rotation (360°) of locking screw 50 may cause the shaft of the screw to traverse a larger axial distance than the axial distance the head of the screw travels seating into the counter thread defined by the fixation hole. As a result, bone plate 10 may deform a distance toward the underlying bone into which locking screw 50 is inserted to accommodate the differential travel length of the shaft relative to the head due to the compression ratio.

FIG. 3 illustrates head 56 having example pitch 64 and shaft 58 having example pitch 66. The compressive force generated by having a differential pitch and/or number of thread starts between the head and shaft can be characterized by the compression ratio as discussed above. In some implementations, locking screw 50 exhibits a compression ratio greater than 1.0, such as greater than 1.5, such as greater than 1.6, greater than 1.7, greater than 1.75, greater than 1.9, greater than 2.1, greater than 2.3, greater than 2.5, or greater than 3.0. For example, the compression ratio of locking screw 50 may be of value falling within a range from 1.45 to 3.5, such as from 1.5 to 2.5. Locking screws exhibiting the foregoing compression ratios may be effective to deform bend 40 of bone plate 10 where the bone plate has a thickness less than 5 mm in the region of the bend, such as less than 3 mm, or less than 2 mm. For example, bone plate 10 may have a thickness ranging from 1 mm to 2 mm (e.g., at least in the region of bend 40) and may be deformed by locking screw having a compression ratio greater than 1.5. In some implementations, a locking screw having any one of the foregoing compression ratios has a single start head threading and a single start shaft threading such that the compression ratio is provided by the shaft thread having a greater pitch than the head thread.

Bone plate 10 can include at least one fixation hole extending through body 12 in the distal region 20 of the bone plate and at least one fixation hole extending through the body and the proximal region 24 of the bone plate. In use, at least two fixation elements can be used to secure the bone plate to two different bone portions, e.g., with intermediate region 28 of the bone plate bridging the joint or gap between the two bone portions. For example, as discussed with respect to FIGS. 1 and 2, bone plate 10 may include at least a first fixation hole 30 and a second fixation hole 34 which, in the illustrated example, further includes a third fixation hole 32 and a fourth fixation hole 36. Bone plate 10 can be secured to underlying bone portions using a single locking screw configured as discussed with respect to FIG. 3, e.g., to interlock with the bone plate and achieve compression, or using multiple locking screws so configured. For example, at least one locking screw configured with an enhanced compression ratio, such as a compression ratio greater than 1.5, (e.g., at least two locking screws so configured) may be used to secure the bone plate to underlying bone portions. One or more other fixation elements having a configuration different than locking screw 50 with an enhanced compression ratio may be inserted through the other fixation holes of the bone plate. When using two or more locking screws 50, the two or more locking screws may have the same configuration as each other (e.g., same compression ratio) or may have different configurations (e.g., different compression ratios) still consistent with locking screw 50 as described herein.

A bone plating system that includes bone plate 10 may include at least one locking screw 50 (e.g. such as two, three, or four locking screws 50) exhibiting a compression ratio effective to deform the bend 40 in the bone plate during use. The bone plating system may include one or more other mechanical fixation elements having a different configuration than locking screw 50 that is insertable through the other fixation holes of the bone plate to complete attachment to the underlying bone portions. Any suitable fixation elements can be used for these other attachment elements, such as screws having a different configuration than locking screw 50, pins, rivets, spikes, or the like.

For example, the bone plating system may include at least one locking screw 50 exhibiting a compression ratio effective to deform the bend in bone plate 10 during use and at least one other screw (e.g., such as two, three, four or more) screws that are nonlocking screws and/or locking screws exhibiting a compression ratio less than that of locking screw 50. For example, the bone plating system may include one or more locking screws having a compression ratio less than 1.5, such as less than 1.45, less than 1.25, or less than 1.2. For example, the bone plating system may include one or more locking screws having a compression ratio that is at least 0.05 less than the compression ratio exhibited by locking screw 50 configured as described with respect to FIG. 3, such as at least 0.1 less, at least 0.25 less, or at least 0.5 less. In some examples, the bone plating system may include one or more locking screws having a compression ratio of 1.0.

In one implementation, a bone plating system includes a bone plate 10, at least two locking screws 50 exhibiting a compression ratio effective to deform bend 40 in the bone plate, and at least two additional locking screws having a compression ratio less than that of locking screw 50 (e.g., a compression ratio that does not result in substantial bending or any bending of the bone plate). In these systems, at least one locking screw 50 may be installed through a fixation hole on the distal region 20 of bone plate 10 and at least one locking screw 50 may be installed through fixation hole on the proximal region 24 of the bone plate. In these examples, the at least one two other locking screws having lower compression ratios than locking screw 50 may be installed through the remaining fixation holes on the distal region 20 and/or proximal region 24 of the bone plate.

Figure 4:
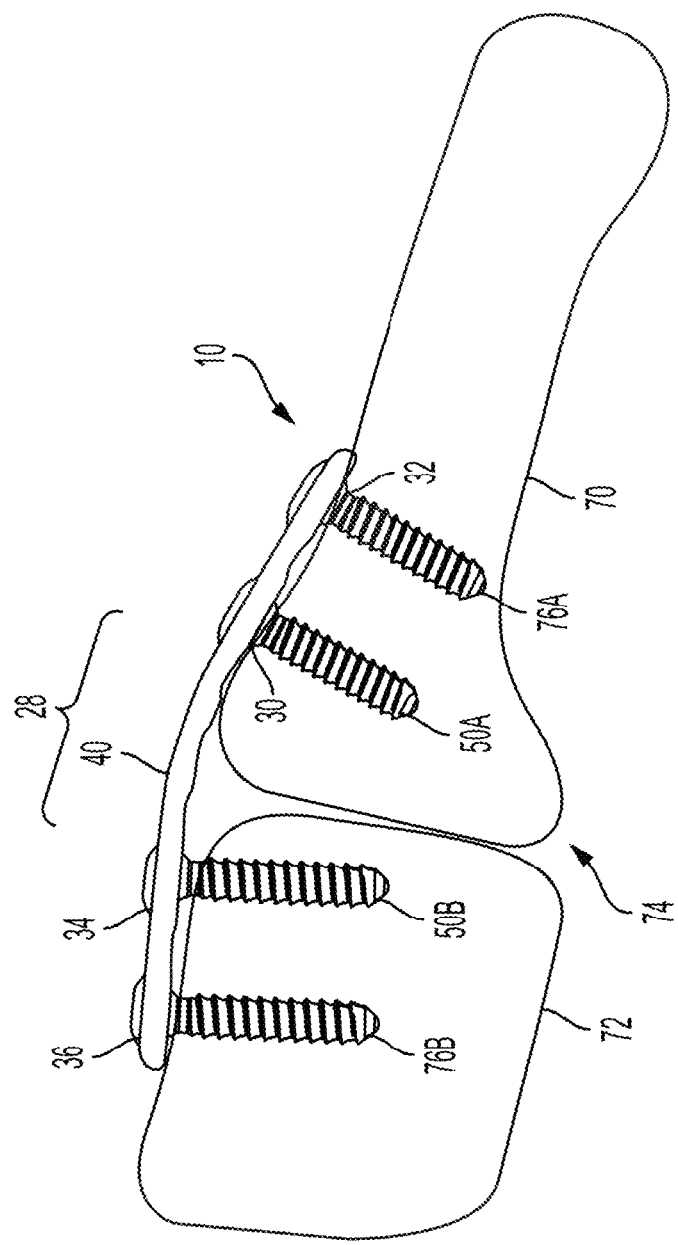
FIG. 4 is an illustration of the example bone plate of FIGS. 1 and 2 secured to a first bone portion and a second bone portion across a joint between the two bone portions.

FIG. 4 is an illustration of bone plate 10 secured to a first bone portion 70 and a second bone portion 72 across a separation 74 between the two bone portions (referred to herein as "joint 74" for purposes of discussion). First bone portion 70 and second bone portion 72 may be different portions of the same bone (e.g., a metatarsal) in which case separation 74 may be a cut line (e.g., where an osteotomy or bone shortening was performed) or fracture between the two bone portions. Alternatively, first bone portion 70 and second bone portion 72 may be different bones in which case separation 74 may be a joint, such as a metatarsal bone and a cuneiform bone separated by a tarsometatarsal joint. In the specific example of FIG. 4, first bone portion 70 is illustrated as a metatarsal and second bone portion 72 is illustrated as a cuneiform.

It should be appreciated that reference to first, second, third, etc. for different features or elements in the disclosure is for purposes of convenience and is not intended to impose an order of operation unless otherwise specified. For example, while bone plate 10 is described as including a first fixation hole 30 positionable over first bone portion 70 and a second fixation hole 34 positionable over second bone portion 72, it should be appreciated that the first bone portion may be a metatarsal or a cuneiform in different examples. Further, during installation, the initial screw may be placed through second fixation hole 34 instead of first fixation hole 30. Accordingly, other orders of installation and arrangement of components can be used and should not be limited to the specific examples described.

In the example of FIG. 4, bone plate 10 is illustrated bridging across the joint 74 with first fixation hole 30 and third fixation hole 32 positioned over an underlying first bone portion 70 (e.g., metatarsal) and second fixation hole 34 and fourth fixation hole 36 positioned over an underlying second bone portion 72 (e.g., cuneiform). When bone plate 10 is installed using at least one locking screw 50 and at least one other fixation element not configured as locking screw 50 (e.g., a non-locking screw or locking screw with lower compression ratio) the at least one locking screw can be inserted through any one of the fixation holes in the bone plate. That said, in some implementations, locking screw 50 may be installed through one or both fixation holes closest to joint 74 separating the two bone portions.

For example, when configured as illustrated in FIG. 4, one locking screw 50A may be installed through first fixation hole 30 and/or one locking screw 50B may be installed through second fixation hole 34. Locking screws 50A, 50B may exhibit a compression ratio effective to deform plate 10 at least in the region of bend 40. Utilizing one or more locking screws with a comparatively high compression ratio through one or more fixation holes closest to intermediate region 28 containing the apex of bend 40 may be useful to help deform the bend toward the underlying bone surfaces, e.g., by delivering the compression closest to where the bone plate is desirably deformed.

One or more other fixation holes of bone plate 10, such as one or more fixation holes positioned proximally and/or distally of those fixation holes closest to intermediate region 28 may be secured to the underlying bone portions using screws having a different configuration than locking screw 50A, 50B. For example, one locking screw 76A may be installed through third fixation hole 32 and/or one locking screw 76B may be installed through fourth fixation hole 36. Locking screws 76A, 76B may exhibit a lower compression ratio than each of locking screws 50A and 50B (e.g., when at least two locking screws 50 are utilized).

A bone plating system that includes a nonplanar bone plate, such as bone plate 10 with bend 40, and one or more locking screws 50 that can interlock with the bone plate and generate a compressive force sufficient to deform the non-planarity of the bone plate during installation, can be useful to help compress the bone portions fixated together using the bone plate. When bone plate 10 is initially positioned over a joint separating two bone portions with the distal region 20 at least partially contacting first bone portion 70 and the proximal region 24 at least partially contacting the second bone portion 72, a gap may exist between the bone facing-surface of the bone plate and the underlying bone portions. As the one or more locking screws 50 are installed through one or more corresponding fixation holes of the bone plate 10 into underlying bone, bend 40 may deform (e.g., plastically and/or elastically) toward the underlying bone portions. This can create a residual spring force compressing the ends of the bone portions together. For example, physically compressing bend 40 from an initial apex height to a reduced apex height may place to the top side of the bone plate in compression and the underside of the bone plate in tension, creating a moment force of asymmetrically distributed magnitude across the end faces of the bones being compressed. In implementations where the bone plate system is applied on a dorsal side of two bone portions (e.g., across a metatarsophalangeal joint or across a tarsometatarsal joint), this may have a tendency to plantarflex the distal bone portion relative to the proximal bone portion, thereby compressing the bone ends across the joint to promote healing (e.g., fusion) and reinforcing a joint realignment performed prior to fixation.

Figure 5:
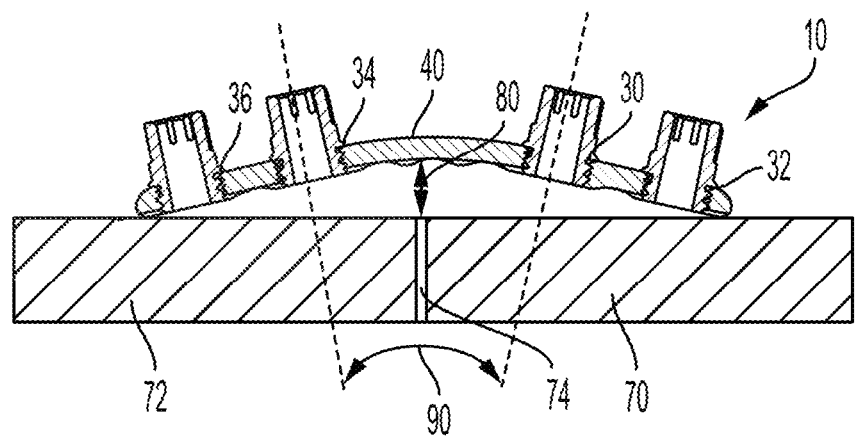
FIGS. 5, 6A and 6B are illustrations showing an example application of the bone plate of FIGS. 1 and 2 using first and second locking screws.
Figure 6A:
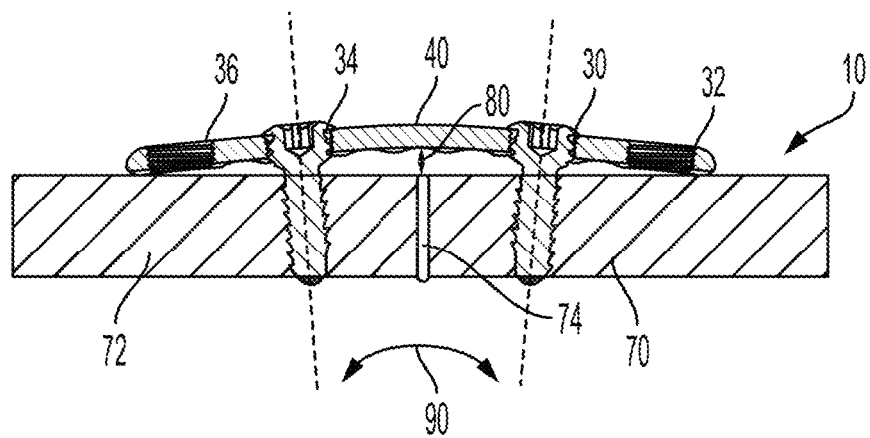
Figure 6B:
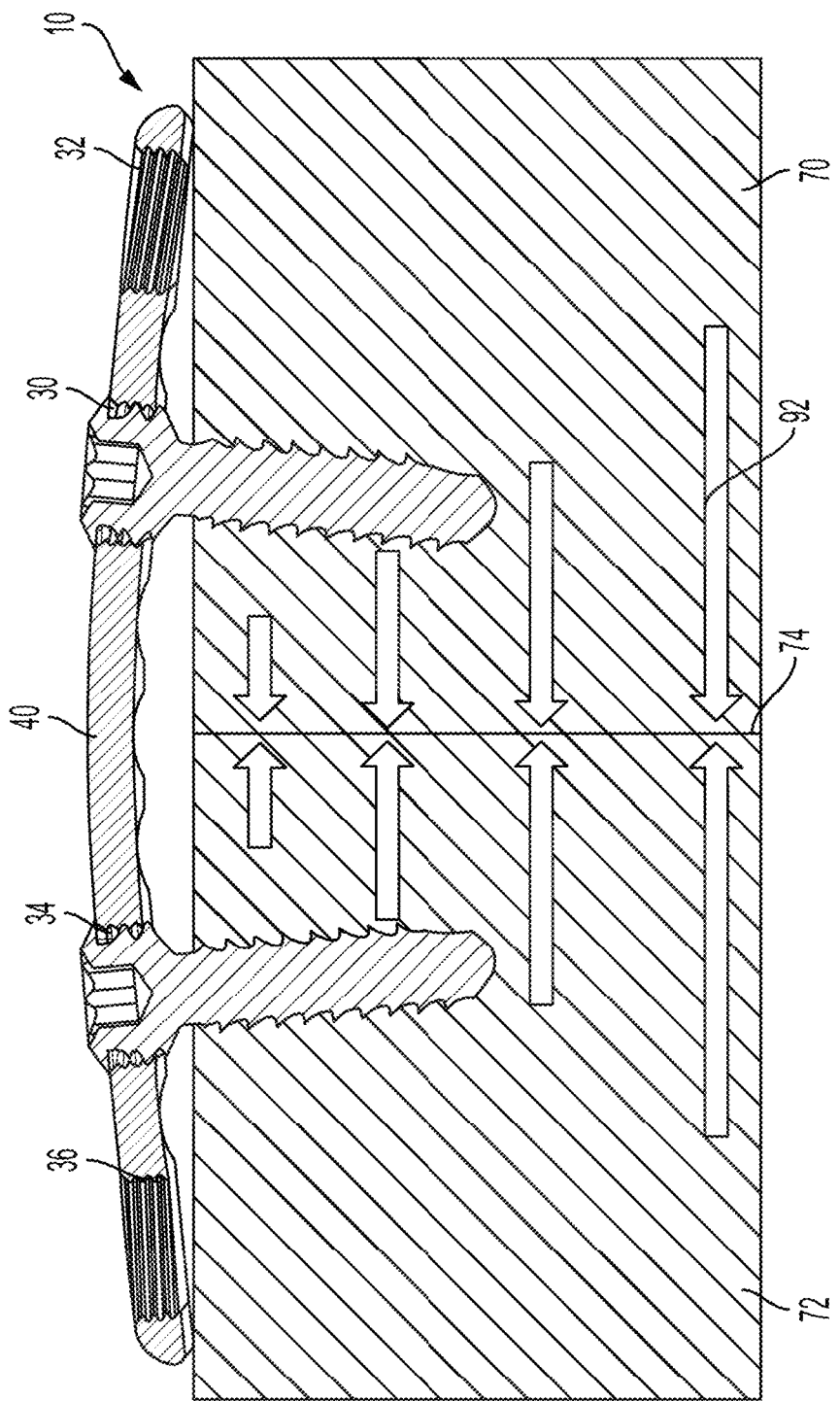

FIGS. 5, 6A and 6B are illustrations showing an example application of bone plate 10 using first and second locking screws 50A, 50B. FIG. 5 illustrates bone plate 10 positioned over a joint 74 (e.g., tarsometatarsal joint) separating a first bone portion 70 (e.g., first metatarsal) from a second bone portion 72 (e.g., medial cuneiform) prior to installation of the locking screws. FIG. 6A illustrates bone plate 10 after installation of first and second locking screws 50A, 50B. FIG. 6B is a force diagram schematically illustrating an example distributed load that may be applied by bone plate 10 across the joint after deformation. Bone plate 10 in FIG. 5 is illustrated with optional drill guides screwed within the fixation holes of the bone plate.

During installation, bone plate 10 can be positioned across joint 74, e.g., with the apex of bend 40 substantially centered over the joint. First fixation hole 30 may be positioned over an underlying first bone portion 70, and second fixation hole 34 may be positioned over an underlying second bone portion 72. For example, distal region 20 may at least partially contact first bone portion 70 and proximal region 24 may at least partially contact second bone portion 72 with bend 40 elevated above the surface of one or both bone portions. As a result, a gap 80 may exist between bone-facing surface 18 of bone plate 10 and the joint line defined by the ends of the bones underneath bend 40. The size of gap 80 may vary, e.g., depending on the extent of bend 40, and in some examples is at least 1 mm, such as at least 1.5 mm, at least 1.75 mm, at least 2 mm, at least 2.25 mm, at least 2.5 mm, at least 3 mm, at least 3.5 mm, at least 4 mm, or at least 5 mm.

The clinician may attach bone plate 10 to the first and second bone portions 70, 72 by inserting one or more locking screws 50A, 50B through one or more corresponding fixation holes of the bone plate. For example, the clinician may insert a first locking screw 50A through first fixation hole 30 and screw the locking screw into the underlying first bone portion 70. The clinician may continue advancing first locking screw 50A until the head thread on the locking screw is partially but not fully engaged with the counter threading extending around first fixation hole 30 (e.g., such that the head threading on the locking screw is partially engaged with the counter threading but can continue to be advanced downwardly relative to the counter threading). If the opposite side of bone plate 10 is already secured to second bone portion 72 using a fixation element, the clinician may further screw first locking screw 50A into first bone portion 70. As the shaft thread of first locking screw 50A advances down into first bone portion 70 after the head thread of the locking screw is initially engaged with the counter thread on the fixation hole, the compression ratio provided by the differential configuration of the head and shaft thread may generate a compressive force that causes bend 40 to deform towards joint 74.

Depending on the order of operation, before or after installing first locking screw 50A into first bone portion 70, the clinician may insert a second locking screw 50B through second fixation hole 34 and screw the locking screw into the underlying second bone portion 72. The clinician may continue advancing second locking screw 50B until the head thread on the locking screw is partially or fully engaged with the counter threading extending around second fixation hole 34 (e.g., such that the head threading on the locking screw is partially engaged with the counter threading but can continue to be advanced against the counter threading or is fully seated with the locking threading). The clinician may further screw second locking screw 50B into second bone portion 72. As the shaft thread of second locking screw 50B advances down into second bone portion 72 after the head thread of the locking screw is initially engaged with the counter thread on the fixation hole, the compression ratio provided by the differential configuration between the head and shaft thread may generate a compressive force that causes bend 40 to deform (e.g., further deform) towards joint 74.

As bend 40 of bone plate 10 deforms towards the facing surfaces of the underlying bone portions and/or joint 74, the bend may flatten. For example, when the bend 40 is characterized by a radius of curvature, the radius of curvature may be smaller when the bend is undeformed (FIG. 5) and larger when the bend is deformed (FIG. 6A) after installation as compared to prior to installation. In some installations, bend 40 of bone plate 10 is bowed down to the facing surface of the underlying bone portions until the bone-facing surface of the bone plate contacts the bone portions in the region formally defining the apex of the bend. In other installations, such as that shown in FIG. 6A, bend 40 of the bone plate is bowed toward the facing surface of the underlying bone portions but a residual gap 80 remains between bone-facing surface 18 of bone plate 10 and the joint line defined by the ends of the bones underneath bend 40. In some examples, the size of gap 80 after installation of bone plate 10 may be less than 2 mm, such as less than 1.75 mm, less than 1.5 mm, less than 1 mm, less than 0.75 mm, or less than 0.5 mm.

As shown in FIGS. 5 and 6, first fixation hole 30 and second fixation hole 34 may be oriented relative to each other such that axes extending through a geometric center of each fixation hole converge to define a converging angle 90. After installation of screws through the first and second fixation holes 30, 34 angle 90 may decrease representing a flattening of bend 40. However, the first and second fixation holes and, correspondingly, first and second screws through the fixation holes, may be angled at a converging angle relative to each other. This may be useful to help generate a force pressing an end of the first bone portion 70 against an end of the second bone portion 72, with the force having a distributed magnitude that is greater on a portion of the bone portions opposite a side against which bone plate 10 is positioned (e.g., on an opposite cortex of the bone portions) and less on a side against which the bone plate is positioned.

In some examples, a difference in angle 90 prior to deformation minus angle 90 prior after deformation is 90 degrees or less, such as 60 degrees or less, 45 degrees or less, 30 degrees or less, or 20 degrees or less. For example, angle 90 prior to deformation may range from 15 degrees to 90 degrees, such as from 20 degrees to 45 degrees. After deformation, angle 90 may range from 0 degrees to 45 degrees, such as from 5 degrees to 15 degrees. In one specific example, angle 90 may be within a range from 20 to 30 degrees prior to deformation and may be in a range from 5 to 15 degrees after deformation.

As the bend or arch in bone plate 10 is physically deformed toward a flattened or unbent profile (e.g., resulting in a complete flattening of the plate or a residual bend or arch of smaller height after deformation), an underside of the plate may be placed in tension and a topside of the plate placed in compression. As a result, a moment force may be applied that has an asymmetrically distributed magnitude across the end faces of the bones being compressed. FIG. 6B illustrates an example triangular distributed load profile that may be created across the end faces of the bone portions by deformation of the bone plate. An asymmetrically distributed force pressing the end faces of the bone portions together may be greater on a side (e.g., a cortex) of the bone portions opposite the side in contact with bone plate 10 than a side (e.g., a cortex) of the bone portions no the side in contact with the bone plate. FIG. 6B illustrates the example asymmetric force distribution with force vectors 92 of different magnitude across the depth of the joint between the two bone portions.

Features described as screws, including locking screw 50, can be formed of any suitable biocompatible material or combinations of materials, such as stainless steel, nitinol, titanium, and/or polymeric materials (e.g., polyether ether ketone or PEEK). The screws may be single axial screws and/or polyaxial screws. Further, the screws may be cannulated or non-cannulated and/or may be self-tapping or non-self-tapping. In some examples, one or more of the screws are cannulated (e.g., all of the screws). In other examples, one or more of the screws are non-cannulated (e.g., all of the screws).

The screws, including locking screw 50, and bone plate 10 may be sized based on the desired application for the plating system. In some examples, each screw used with bone plate 10 is sized to be inserted into a metatarsal and/or cuneiform of a human foot. For example, each screw may have a length ranging from 8 mm to 18 mm, such as from 10 mm to 16 mm, or from 12 mm to 14 mm. When provided with screws intended to be inserted into both the metatarsal and cuneiform, the screws may be the same size, or one may be longer than the other (e.g., by 1 mm, 2 mm, or more). Although the diameter of the shaft of the screws may vary, in some examples, the diameter ranges from 2 mm to 4 mm, such as from 2.5 mm to 3.2 mm.

Figure 7:
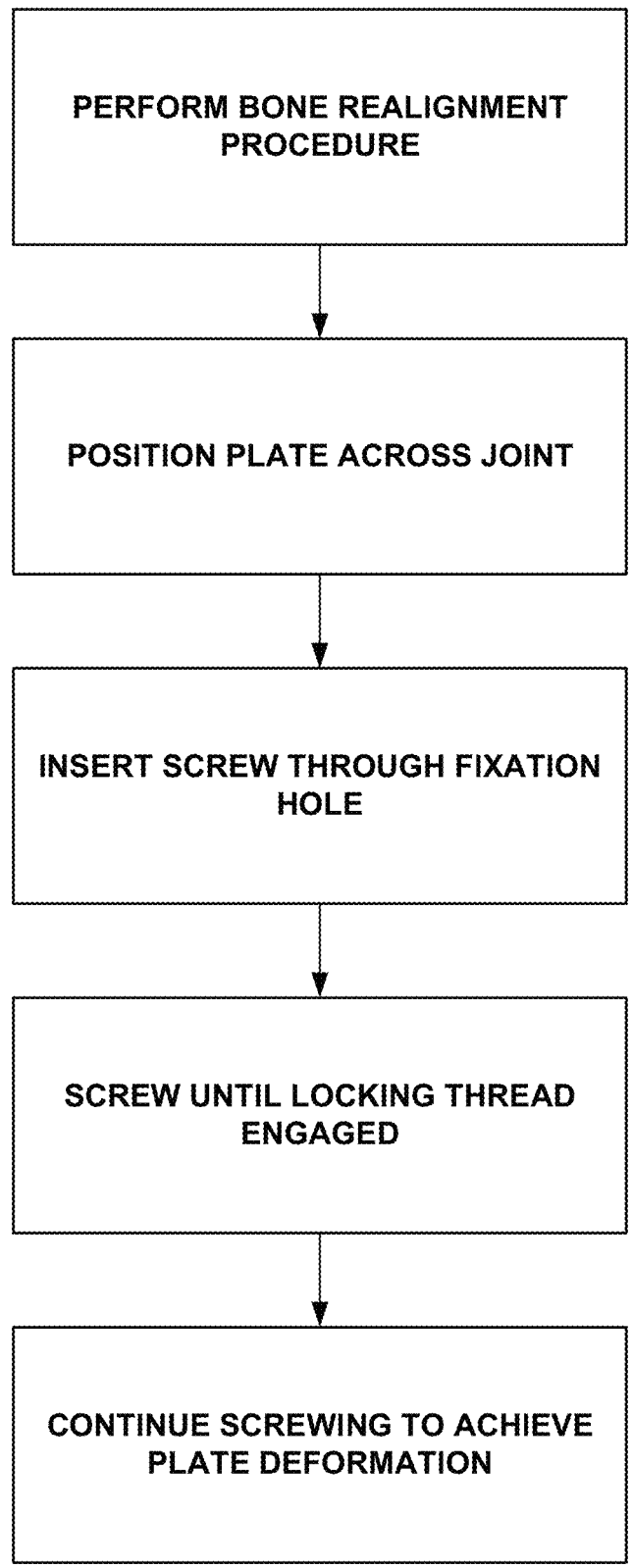
FIG. 7 is a flow diagram illustrating an example technique for attaching a bone plate system according to disclosure.

FIG. 7 is a flow diagram illustrating an example technique for attaching a bone plate system according to disclosure. The technique of FIG. 7 involves performing an optional bone realignment procedure to realign a first bone portion 70 relative to a second bone portion 72, which is then fixated using the bone plate system (100). The bone realignment procedure may involve realigning a metatarsal relative to a cuneiform, such as a first metatarsal relative to a medial cuneiform, or may involve realigning other bone portions relative to each other. For example, the bone realignment procedure may involve realigning a second metatarsal relative to an intermediate cuneiform, a third metatarsal relative to a lateral cuneiform, a proximal phalanx relative to a metatarsal across a metatarsophalangeal joint, or yet other bone portions relative to each other.

To correct an alignment of a first bone portion (e.g., metatarsal) relative to a second bone portion (e.g., cuneiform), for example, the clinician may surgically access the joint between the two bone portions. Once accessed the clinician may prepare end faces of the two bone portions. The clinician can prepare the end of each bone so as to promote fusion of the bone ends across the joint following realignment. Bone preparation may involve using a tissue removing instrument to apply a force to the end face of the bone so as to create a bleeding bone face to promote subsequent fusion. Example tissue removing instruments that can be used include, but are not limited to, a saw, a rotary bur, a rongeur, a reamer, an osteotome, a curette, and the like. The tissue removing instrument can be applied to the end face of the bone being prepared to remove cartilage and/or bone. For example, the tissue removing instrument may be applied to the end face to remove cartilage (e.g., all cartilage) down to subchondral bone. Additionally or alternatively, the tissue removing instrument may be applied to cut, fenestrate, morselize, and/or otherwise reshape the end face of the bone and/or form a bleeding bone face to promote fusion. In instances where a cutting operation is performed to remove an end portion of a bone, the cutting may be performed freehand or with the aid of a cutting guide having a guide surface positionable over the portion of bone to be cut. When using a cut guide, a cutting instrument can be inserted against the guide surface (e.g., between a slot define between two guide surfaces) to guide the cutting instrument for bone removal.

Either before or after preparing one or both ends of the bone portions, the clinician may move one bone portion (e.g., the metatarsal) in at least one plane, such as at least the transverse plane to close an intermetatarsal angle between the bone portion (e.g., a first metatarsal) and an adjacent bone (e.g., a second metatarsal) and/or a frontal plane to reposition the sesamoid bones. In some examples, the clinician moves the bone portion in multiple planes, such as the transverse plane and/or frontal plane and/or sagittal plane. The clinician may or may not utilize a bone positioning guide to facilitate movement of the bone portion. With the bone portion moved to a desired position, the clinician can optionally provisionally fixate the moved position (e.g., by inserting a k-wire through the moved bone portion into an adjacent bone portion) and then permanently fixate the moved position using one or more bone plate systems as described herein. Details on example bone realignment instruments and techniques that can be used in conjunction with the present disclosure are described in U.S. Pat. No. 9,622,805, issued Apr. 18, 2017 and entitled "BONE POSITIONING AND PREPARING GUIDE SYSTEMS AND METHODS," the entire contents of which are incorporated herein by reference.

In some applications, independent of whether the clinician performs the specific bone realignment technique discussed above, the clinician temporarily or provisionally fixates first bone portion 70 relative to second bone portion 72 prior to attaching bone plate 10 across the joint separating the two bone portions. The clinician may press the end faces of first bone portion 70 and second bone portion 72 together, e.g., with hand pressure and/or using compressing instrument physically attached to both the first bone portion and the second bone portion. For instance, the clinician may attach compressing instrument to the first bone portion 70 with one or more fixation pins and also attach the compressing instrument to the second bone portion using one or more fixation pins. The compressing instrument may have a mechanism (e.g., threaded rod, rack and pinion) that presses against the pins inserted through the two bone portions to compress the end faces of the two bone portions together. Additional details on example compressing instruments that may be used can be found in US Patent Publication No. 2020/0015856, published Jan. 16, 2020 and entitled "COMPRESSOR-DISTRACTOR FOR ANGULARLY REALIGNING BONE PORTIONS," the entire contents of which are incorporated herein by reference.

In some implementations, the clinician inserts one or more fixation pins through the end faces of the first bone portion 70 and second bone portion 72 in addition to or in lieu of compressing the end faces with a compressing instrument. The fixation pin may be a k-wire, olive wire (e.g., pin with region of enlarged cross-section) or other fixation pin structure. The fixation pin crossing joint 74 between first bone portion 70 and second bone portion 72 can help provisionally fixate and/or compress the end faces of the two bone portions together prior to installation of bone plate 10 for permeant fixation (and subsequent fusion of the bone faces together). When used, the one or more fixation pins can be removed from the end faces of the two bone portions and across the joint between the bone portions after installation of bone plate 10 (e.g., after installation of at least one fixation element through the bone plate into each of first bone portion 70 and second bone portion 72).

With further reference to FIG. 7, the example technique includes positioning a bone plate 10 across a joint separating two bone portions (102). The bone plate 10 can include first fixation hole 30, second fixation hole 34, and bend 40 between the first fixation hole and the second fixation hole. Positioning the bone plate across the joint may involve positioning bend 40 over the joint, e.g., with distal region 20 of the bone plate contacting the first bone portion and the proximal region 24 of the bone plate contacting the second bone portion. As a result of the presence of the bend, a gap 80 may exist between the bone facing surface 18 of the bone plate and the underlying surfaces and/or joint of the bone ends.

The technique of FIG. 7 may also involve inserting a locking screw 50 through a first fixation hole of the bone plate (104). The locking screw 50 can have a head with a head thread and a shaft with a shaft thread. The shaft thread may be configured relative to head thread to provide a compression ratio greater than 1.0, such as greater than 1.5. The head thread may be configured (e.g., size and/or shaped) to engage with corresponding counter threading encircling the first fixation hole. The clinician may insert the locking screw through the first fixation hole by advancing the distal end of the screw through the opening defined by the first fixation hole and beginning to screw the shaft of the locking screw into the underlying bone. In different examples, a hole may or may not be predrilled into the bone prior to insertion of the screw.

With the distal end of locking screw 50 inserted through the first fixation hole of bone plate 10, the clinician can screw the locking screw into the underlying bones (106). Operating under hand power or with the aid of a rotary drill instrument, the clinician can rotate locking screw 50 in either a clockwise or counterclockwise direction (depending on the pattern of the thread) so as to advance the screw axially downwardly into the bone portion underlying the fixation hole in the bone plate. The clinician can continue screwing locking screw 50 and advancing the screw axially into the bone portion. When the head thread on the head of locking screw contacts the counter threading encircling the first fixation hole, the head thread may interleave with the counter threading encircling the first fixation hole thereby engaging the threading.

With the head thread at least partially engaged with the counter thread defined by the first fixation hole, the technique of FIG. 7 involves further screwing locking screw 50 into the first fixation hole and into the underlying bone. When the bone plate 10 is already affixed to the other bone portion across the joint, further rotation of locking screw 50 may cause the bone plate (e.g., bend 40 in the bone plate) to deform. The bone plate may deform by bowing toward the joint and underlying bones.

Prior to and/or after installing locking screw 50 through the first fixation hole of the bone plate, the clinician can install one or more fixation elements, such as one or more locking screws through one or more additional fixation holes of the bone plate. For example, prior to or after installing locking screw 50 through the first fixation hole into the first bone portion, the clinician may install another locking screw (which may or may not have a comparatively high compression ratio) through the second fixation hole into the second bone portion. The clinician may install one or more additional screws, such as one or more additional locking screws (which may or may not have a comparatively high compression ratio) through other fixation holes in the bone plate, such as a third fixation hole and a fourth fixation hole.

A bone plating system applied across a joint separating the ends of two bone portions as described herein can help compress the end faces of the two bone portions together to facilitate fusion. In some examples, the plating system produces asymmetric compression in which the far cortex of the bone ends is compressed more than the near cortex. In some applications, such as when the bone plate is applied to the dorsal surface of the bone portions, this can help plantarflex the realigned bone portion and reinforce a corrective realignment in the sagittal plane while facilitating fusion. Additionally or alternatively, when the bone plate is applied to the medial surface of the bone portions, this can help laterally bias the realigned bone portion and reinforce a corrective realignment in the transverse plane (e.g., bias toward closing the intermetatarsal angel) while facilitating fusion.

A variety of different instruments and additional or alternative techniques can be used to facilitate installation of a bone plating system as described herein. For example, one or more driving pins (e.g., plate tack pins, drill pins) may be used to help facilitate installation of bone plate 10. When used, the driving pin may be inserted through a fixation hole of the bone plate and into the underlying bone. In some examples, the driving pin includes a threaded distal region and can be rotationally driven into the underlying bone via screwing. In either case, the driving pin may enter or bore a hole in the bone portion underlying the fixation hole through which the driving pin is inserted.

In some implementations, the driving pin may include an enlarged region having a larger cross-sectional area than a cross-sectional area of the fixation hole. As the driving pin is advanced into the underlying bone, the region of larger cross-sectional area may press against a top side of bone plate 10 (e.g., either directly against the top side or indirectly via a drill guide extending above the top surface). Continued rotation of the driving pin may cause the enlarged cross-sectional area to deform bend 40 by compressing the bend portion toward the underlying joint and/or surfaces of the bone portions. As a result, the bone plate may be partially or fully deformed toward a desired degree of compression by the driving pin. The driving pin can then be removed from the fixation hole and a locking screw inserted through the fixation hole and into the underlying bone. Another fixation device, such as a pin, screw, etc. may be placed through one or more adjacent holes prior to removing the driving pin to help hold the compression of the bone plate for installation of the locking screw.

When bone plate 10 is pre-deformed using a driving pin prior to installation of one or more screws, the screws used to affix the bone plate to the underlying bone portions may or may not include locking screw 50 exhibiting a comparatively high compression ratio. In some applications using a driving pin for pre-deformation, at least one (and optionally all) fixation elements used to secure the deformed bone plate to the underlying bone may be non-locking screws or locking screws configured with a lower compression ratio (e.g., one not effective to substantially deform the plate upon installation, such as compression ratio less than 1.5, or a compression ratio of 1.0). That said, in some implementations, locking screw 50 with an enhanced compression ratio may be installed (e.g., through one or both fixation holes closest to joint 74) to help affix the bone plate to the underlying bone portions.

Figure 8:
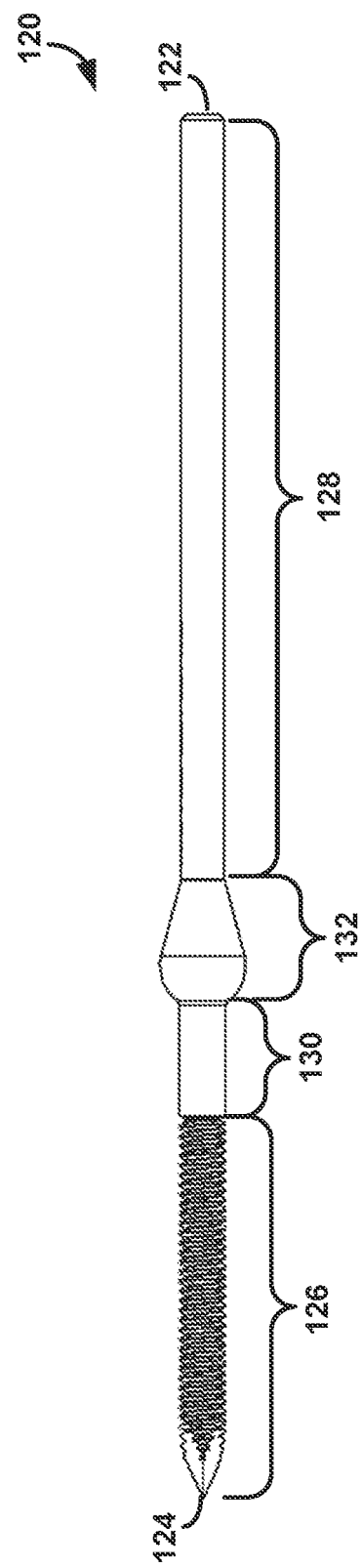
FIG. 8 is side view of an example driving pin that can be used to help install a bone plate on a bone.

FIG. 8 is side view of an example driving pin 120 that can be used to help install a bone plate on a bone. For example, driving pin 120 may be connected to a driver (e.g., impact driver, rotary driver, drill) that uses driving pin 120 to impart a force for opening a hole in a bone underlying a bone plate. Additionally or alternatively, a clinician utilizing driving pin 120 can apply a force through a hand-powered instrument to drive the driving pin. In either case, after creating the hole and/or orienting the bone plate using driving pin 120, the driving pin can be removed from the bone and bone plate. A bone fixation member (e.g., bone screw) can then be inserted into the opening created by driving pin 120 to permanently hold the bone plate to the bone.

In the illustrated example, driving pin 120 defines a body that extends from a proximal end 122 to a distal end 124.

The body defines multiple regions of different cross-sectional thickness which, in the illustrated example, is shown as at least three regions of different cross-sectional thickness. For example, the body of driving pin 120 may define a bone penetrating region 126 adjacent the distal end, a driving region 128 adjacent the proximal end, and bone plate orienting region 130 between the bone penetrating region and the driving region. Bone penetrating region 126 can have a smaller cross-sectional thickness than the bone plate orienting region 130. Bone plate orienting region 130 may have a smaller cross-sectional thickness than driving region 128 or, in other implementations, can have the same cross-sectional thickness or a larger cross-sectional thickness than driving region 128.

Configuring driving pin 120 with multiple cross-sectional thicknesses can be useful to provide different functionalities while limiting unnecessary trauma to the bone in which the driving pin is engaged. For example, bone penetrating region 126 can be sized comparatively small to minimize bone damage and ease insertion of the distal end of the driving pin. Bone plate orienting region 130 may be larger and be sized complementary to the dimeter of a fixation hole of the bone plate in which the driving pin is to be inserted. This can provide close conformance between the driving pin and the bone plate, e.g., for accurately rotating the bone plate about the driving pin to orient the bone plate during installation. Driving region 128 may be larger and sized for engagement with a driver to be used in the process. In some configurations, driving pin 120 is provided as part of a kit that includes other driving instruments (e.g., pins, k-wires) and has the same diameter as one or more of those other instruments to provide a uniform driving connection size across the instruments. In other words, driving pin 120 may be part of a kit (e.g., where all the components of the kit art contained in a sterile case) having one or more (and optionally two or more) other instruments, each having a substantially same diameter shaft and each being configured to couple to a same driver for driving the instruments.

As shown in FIG. 8, bone penetrating region 126 may be threaded to facilitate rotationally driving (screwing) the driving pin into the underlying bone. When threaded, the threading on bone penetrating region 126 may define any suitable pitch which may be the same as, or different than, the pitch on the shaft thread of locking screw 50 that can be inserted through the fixation hole after removal of the driving pin. Distal end 124 of driving pin 120 may have a trocar or other tip (e.g. self-tapping tip) for starting penetration of driving pin 120 into the underlying bone.

Although driving pin 120 is illustrated as including a threaded bone penetrating region 126 and an unthreaded plate orienting region 130, the driving pin need not have the two distinct regions. Rather, when bone penetrating region 126 and plate orienting region 130 are configured with the same cross-sectional size, the threading may optionally extend to also encompass the region of the driving pin that functions as the plate orienting region.

In general, driving pin 120 can have any have desired cross-sectional shape, including polygonal shapes, arcuate shapes, and combinations thereof. In some configurations, at least bone penetrating region 126, driving region 128, and bone plate orienting region 130 of the driving pin have a circular cross-sectional shape.

While driving pin 120 have a variety of different sizes, in some examples, bone penetrating region 16 has a diameter ranging from 0.1 mm to 2 mm and/or bone plate orienting region 130 has a diameter ranging from 0.5 to 3 mm and/or driving region 128 has a diameter ranging from 1.6 mm to 3.7 mm. For example, bone penetrating region 126 may have a diameter ranging from 1 mm to 2 mm, and bone plate orienting region 130 may have a diameter ranging from 1 mm to 2 mm.

Driving pin 120 can have one or more regions of different cross-sectional thickness than bone penetrating region 126, driving region 128, and bone plate orienting region 130. For example, in the illustrated example, driving pin 120 includes a fourth region 132 of greater cross-sectional thickness than at least bone penetrating region 126 and bone plate orienting region 130. In the illustrated configuration, fourth region 132 also has a cross-sectional thickness greater than driving region 128. Fourth region 132 is positioned proximally of bone plate orienting region 130 and can have a cross-sectional thickness greater than that of a bone plate fixation hole diameter and/or drill guide into which driving pin 120 is configured to be inserted. Fourth region 132 can function as a feature that limits that downward insertion depth of driving pin 120 as it is being inserted through a bone plate and/or drill guide. When included, fourth region 132 may be integral (e.g. permanently formed with) a remainder of the driving pin body or may be part of a multi-piece assembly that is separately attachable to the driving pin.

Fourth region 132 can have any desired cross-sectional shape (e.g., round, spherical, rectangular, triangular, elliptical), and the cross-sectional shape may be the same as or different than that of adjacent sections of the driving pin. In some examples, fourth region 132 has a cross-sectional thickness ranging from 1.5 mm to 12 mm, such as from 2 mm to 5 mm. Additional details on example driving pin techniques and devices that may be used are described in US Patent Publication No. 2020/0015870, filed Jul. 12, 2019 and titled "MULTI-DIAMETER BONE PIN FOR INSTALLING AND ALIGNING BONE FIXATION PLATE WHILE MINIMIZING BONE DAMAGE, the entire contents of which are incorporated herein by reference.

Figure 9:
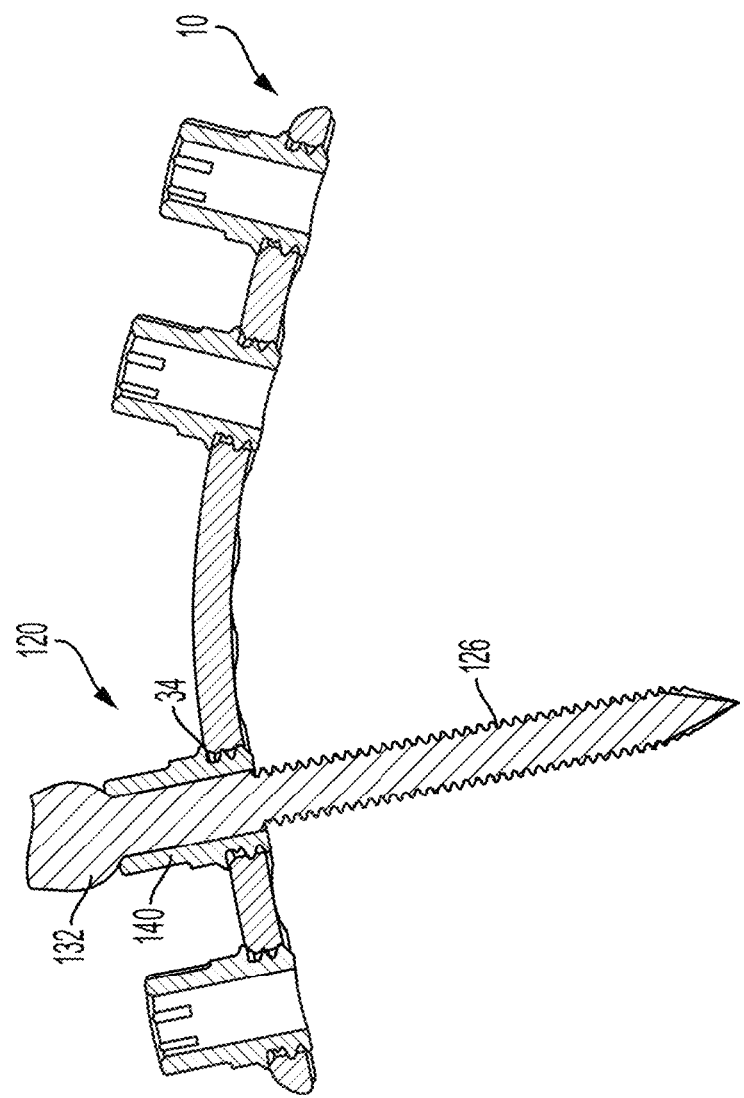
FIG. 9 is a side view of an example bone plate illustrating an example driving pin of FIG. 8 inserted through a fixation hole of the bone plate.

FIG. 9 is a side view of bone plate 10 illustrating driving pin 120 inserted through a second fixation hole 34 of the bone plate. In the illustrated configuration, a drill guide 140 is threaded into the threaded opening defined by the fixation hole. As shown in this example, the thread encircling the bone penetrating region terminates at the proximal end prior to where the driving pin intersects the bone plate, when the driving pin is fully inserted and the enlarged region is bearing against the drill guide (or, in other configurations, the top surface of bone plate itself).

FIGS. 10-15 are perspective illustrations showing example procedure steps that may be used to install a bone plate to two bone portions separated by a joint according to the disclosure. In particular, FIGS. 10-15 illustrate example procedure steps for attaching bone plate 10 to a medial cuneiform 70 and a first metatarsal 72 separated by a tarsometatarsal joint, e.g., after performing preparation on the ends of the two bones and realigning the first metatarsal relative to the cuneiform and/or provisionally fixating the bone portions together.

As shown in FIG. 10, bone plate 10 can be positioned across the tarsometatarsal joint separating a metatarsal 72 from cuneiform 70. In the illustrated orientation, bone plate 10 is positioned on the dorsal side of the two bones (e.g., dorsal-most half, dorsal-most quarter). In other applications, bone plate 10 may be positioned at other locations along the surface of the two bones, such as a medial side of the two bones (e.g., medial-most half, medial-most quarter), and/or on a dorsal-medial side of the two bones.

Continuing with FIG. 11, a first driving pin 120A can be inserted through a first fixation hole 30 positioned closest to a region of bone plate 10 defining an apex of the bend. Driving pin 120A can be rotationally driven through the first fixation hole into an underlying bone (cuneiform 70). As the driving pin bores axially down into the bone, the enlarged region of the driving pin can contact the top surface of the bone plate (e.g., the top surface of the drill guide extending above the bone plate). Continued rotation of driving pin 120A can cause the enlarged region of the driving pin to press against the bone plate and at least partially deform the bend by compressing the bend, resulting in a comparative flattening of the bone plate.

Figure 12:
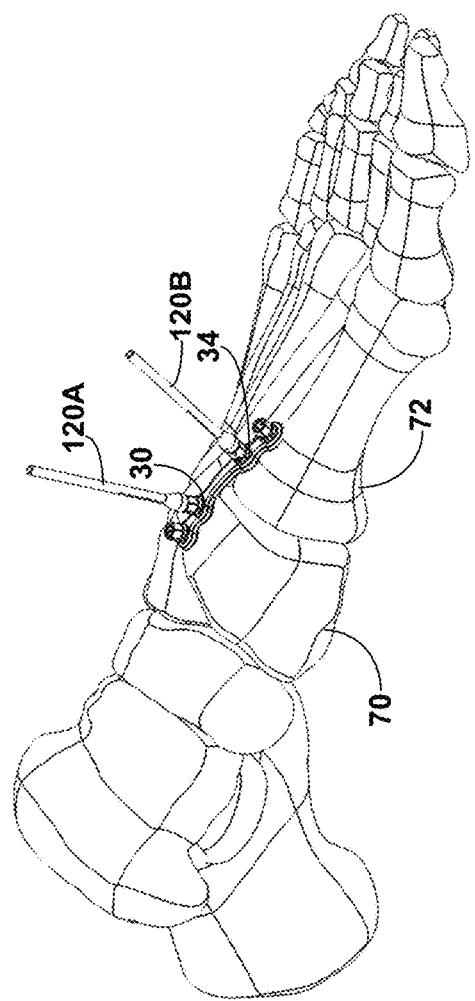

As shown in FIG. 12, a second driving pin 120B can be inserted through a second fixation hole 34 positioned on an opposite side of the joint from first driving pin 120A. Second fixation hole 34 may be positioned closest to the region of bone plate 10 defining an apex of the bend on the opposite side of first fixation hole 30. Second driving pin 120B can be rotationally driven through the second fixation hole into an underlying bone (metatarsal 72). Again, as the driving pin bores axially down into the bone, the enlarged region of the driving pin can contact the top surface of the bone plate (e.g., the top surface of the drill guide extending above the bone plate). Continued rotation of driving pin 120B can cause the enlarged region of the driving pin to press against the bone plate, further deforming the bend in the bone plate initially deformed upon insertion of the first driving pin 120A. Complete insertion of second driving pin 120B may complete deformation of bone plate 10 to a desired degree of compression.

Figure 13:
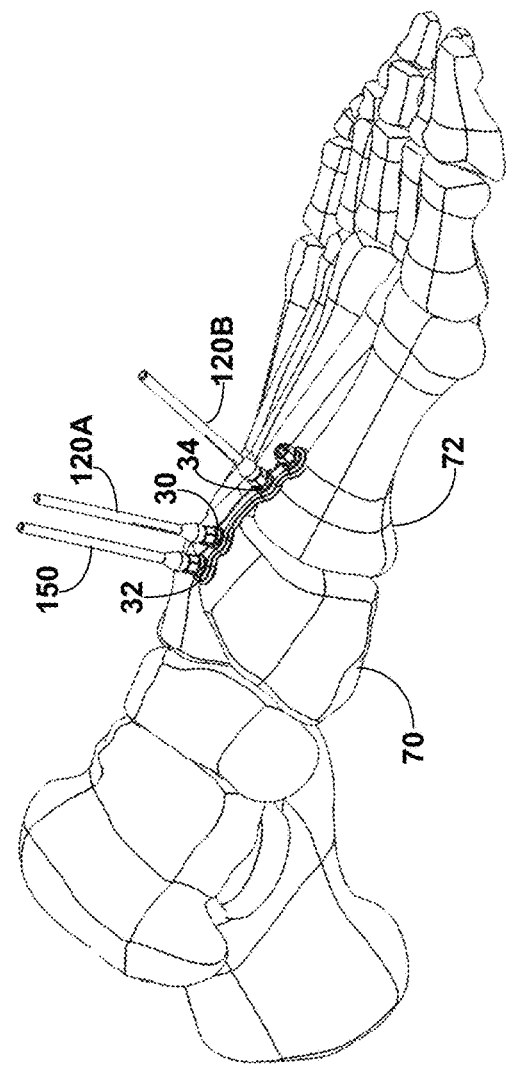

To retain bone plate 10 for insertion of a screw, a third fixation pin 150 can be inserted into an adjacent fixation hole of the bone plate to the fixation hole in which the screw is desirably inserted, as shown in FIG. 13. In this example, third fixation pin 150 is inserted through third fixation hole 32 of bone plate 10 into the underlying bone. Third fixation pin can be configured the same as driving pin 120 or can be a different configuration of pin such as, e.g., a threaded plate tack, in olive drive, or other pin. Third fixation pin 150 can be applied to hold the deformation and compression of bone plate 10 (and the position of the bone plate). In other examples, the technique may proceed without installation of third fixation pin 150. First driving pin 120A may be removed while second fixation pin 120B (or a screw through the opposite fixation hole) remains in place.

Figure 14:
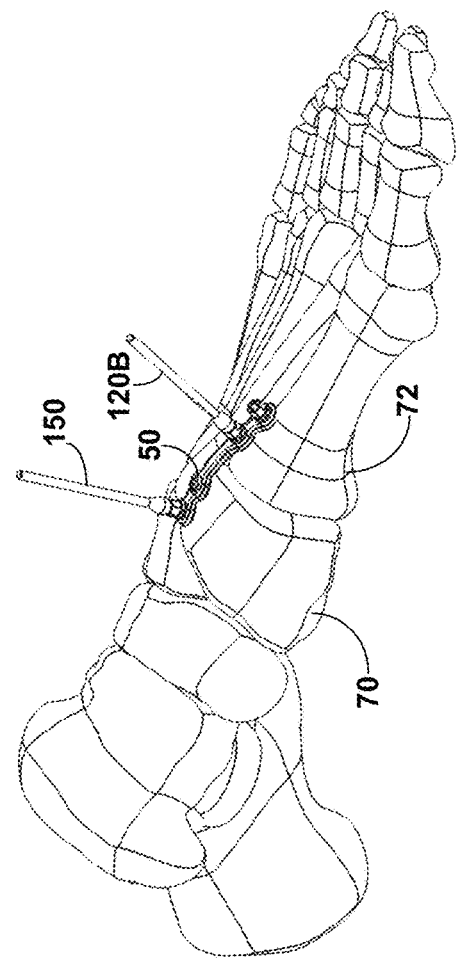

In either case, first driving pin 120A can be removed from first fixation hole 30 to open the fixation hole for installation of a locking screw, as illustrated in FIG. 14. After first driving pin 120A is removed, a locking screw 50 (or other type of fixation element as described herein) can be screwed through first fixation hole 30 into the underlying bone.

With locking screw 50 installed through first fixation hole 30 to secure bone plate 10 to cuneiform 70, third fixation pin 150 (when used) can be removed from the cuneiform. In addition, second driving pin 120B can be removed from metatarsal 72 and a screw screwed through second fixation hole 34 to secure the bone plate to the metatarsal. The screw inserted through second fixation hole 34 can be locking screw 50 or a different type of screw structure or other fixation element as described herein. In some examples, a fixation pin (e.g., third fixation pin 150) is inserted through fourth fixation hole 36 before removing second driving pin 120B.

Figure 15:
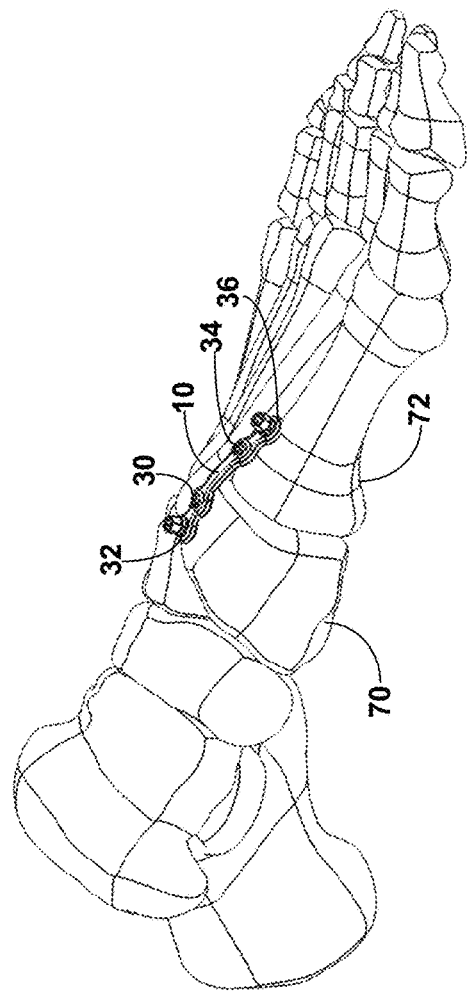

FIG. 15 illustrates bone plate 10 attached across the tarsometatarsal joint separating medial cuneiform 70 from first metatarsal 72. The bone plate is attached to medial cuneiform 70 and first metatarsal 72 with screws inserted through first and second fixation holes 30, 34 of the bone plate. Depending on the configuration of bone plate 10 in the procedure being undertaken, the clinician may proceed to complete attachment of the bone plate, e.g., by installing screws through third fixation hole 32 and fourth fixation hole 36 into the underlying bones.

In some applications, however, the clinician may desire to install multiple bone plates across the joint rather than only installing a single bone plate. The multiple bone plates may be positioned at different locations about the perimeter of the joint so as to provide a biplanar plating construct. In these applications, each bone plate and/or screws may be configured and installed according to the present disclosure, or one bone plate system may be different than the other bone plate system. In some such applications, the clinician may proceed to begin installing the second bone plate before completing installation of the first bone plate. For example, the clinician may proceed to begin installing the second bone plate after securing the first bone plate through the first and second fixation holes 30, 34 but prior to installing screws through other fixation holes (e.g., the third and/or fourth fixation holes 32, 36).

Figure 16:
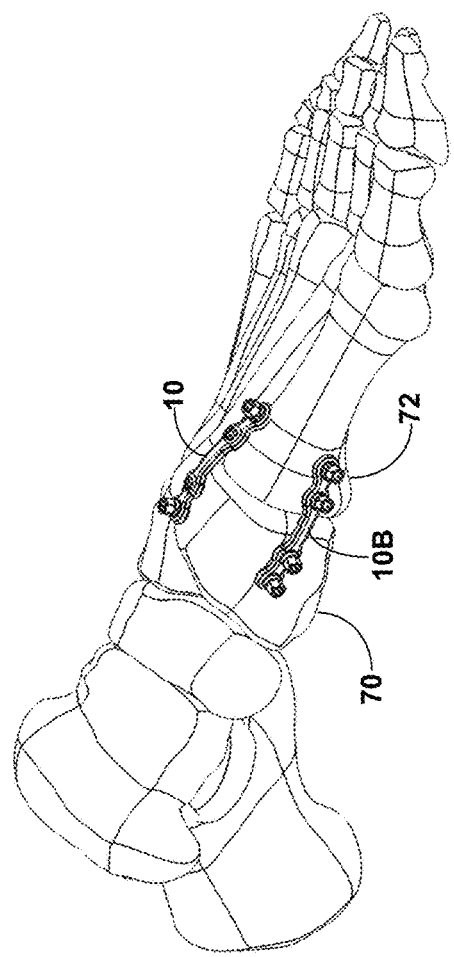

For example, FIGS. 16-22 illustrate example procedural steps that may be performed before, after, or in lieu of the procedure steps described with respect to FIGS. 10-15. As shown in FIG. 16, a bone plate 10B can be positioned across the tarsometatarsal joint separating a metatarsal 72 from cuneiform 70. In the illustrated orientation, bone plate 10B is positioned on the medial side of the two bones (e.g., medial-most half, medial-most quarter) although can be positioned at other locations about the bones.

Figure 17:
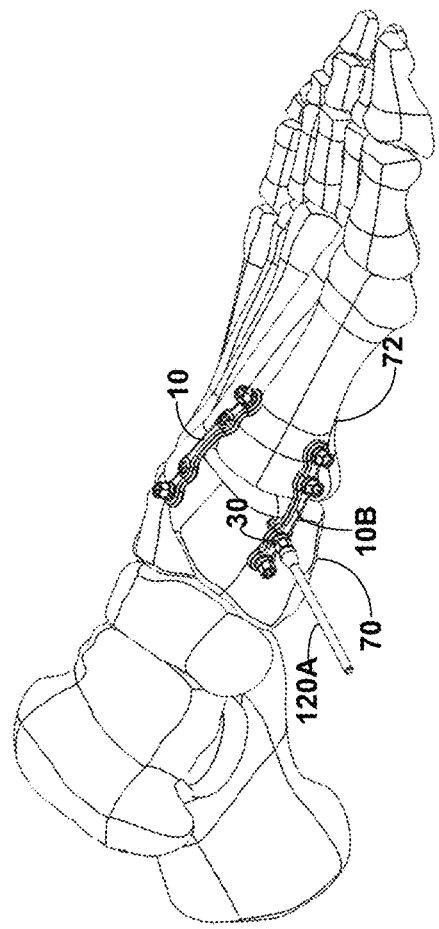

Continuing with FIG. 17, a first driving pin 120A can be inserted through a first fixation hole 30 positioned closest to a region of bone plate 10B defining an apex of the bend. Driving pin 120A can be rotationally driven through the first fixation hole into an underlying bone (cuneiform 70). As the driving pin bores axially down into the bone, the enlarged region of the driving pin can contact the top surface of the bone plate (e.g., the top surface of the drill guide extending above the bone plate). Continued rotation of driving pin 120A can cause the enlarged region of the driving pin to press against the bone plate and at least partially deform the bend by compressing the bend, resulting in a comparative flattening of the bone plate.

As shown in FIG. 18, a second driving pin 120B can be inserted through a second fixation hole 34 positioned on an opposite side of the joint from first driving pin 120A. Second fixation hole 34 may be positioned closest to the region of bone plate 10 defining an apex of the bend on the opposite side of first fixation hole 30. Second driving pin 120B can be rotationally driven through the second fixation hole into an underlying bone (metatarsal 72). Again, as the driving pin bores axially down into the bone, the enlarged region of the driving pin can contact the top surface of the bone plate (e.g., the top surface of the drill guide extending above the bone plate). Continued rotation of driving pin 120B can cause the enlarged region of the driving pin to press against the bone plate, further deforming the bend in the bone plate initially deformed upon insertion of the first driving pin 120A. Complete insertion of second driving pin 120B may complete deformation of bone plate 10B to a desired degree of compression.

To retain bone plate 10 for insertion of a screw, a third fixation pin 150 can be inserted into an adjacent fixation hole of the bone plate to the fixation hole in which the screw is desirably inserted, as shown in FIG. 19. In this example, third fixation pin 150 is inserted through third fixation hole 32 of bone plate 10 into the underlying bone. Third fixation pin can be configured the same as driving pin 120 or can be a different configuration of pin such as, e.g., a threaded plate tack, in olive drive, or other pin. Third fixation pin 150 can be applied to hold the deformation and compression of bone plate 10B (and the position of the bone plate). In other examples, the technique may proceed without installation of third fixation pin 150. First driving pin 120A may be removed while second fixation pin 120B (or a screw through the opposite fixation hole) remains in place.

Figure 20:
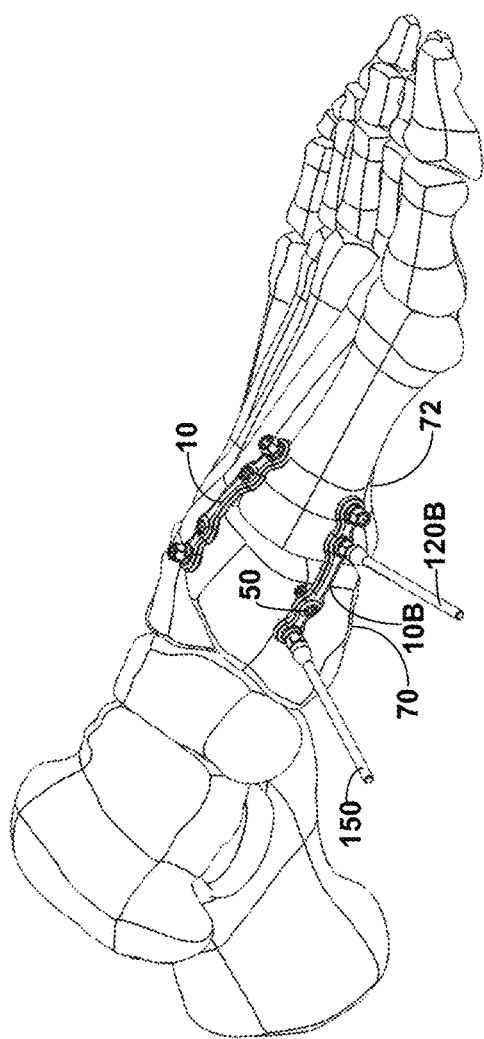

In either case, first driving pin 120A can be removed from first fixation hole 30 to open the fixation hole for installation of a locking screw, as illustrated in FIG. 20. After first driving pin 120A is removed, a locking screw 50 (or other type of fixation element as described herein) can be screwed through first fixation hole 30 into the underlying bone.

With locking screw 50 installed through first fixation hole 30 to secure bone plate 10 to cuneiform 70, third fixation pin 150 (when used) can be removed from the cuneiform. In addition, second driving pin 120B can be removed from metatarsal 72 and a screw screwed through second fixation hole 34 to secure the bone plate to the metatarsal. The screw inserted through second fixation hole 34 can be locking screw 50 or a different type of screw structure or other fixation element as described herein. In some examples, a fixation pin (e.g., third fixation pin 150) is inserted through fourth fixation hole 36 before removing second driving pin 120B.

Figure 21:
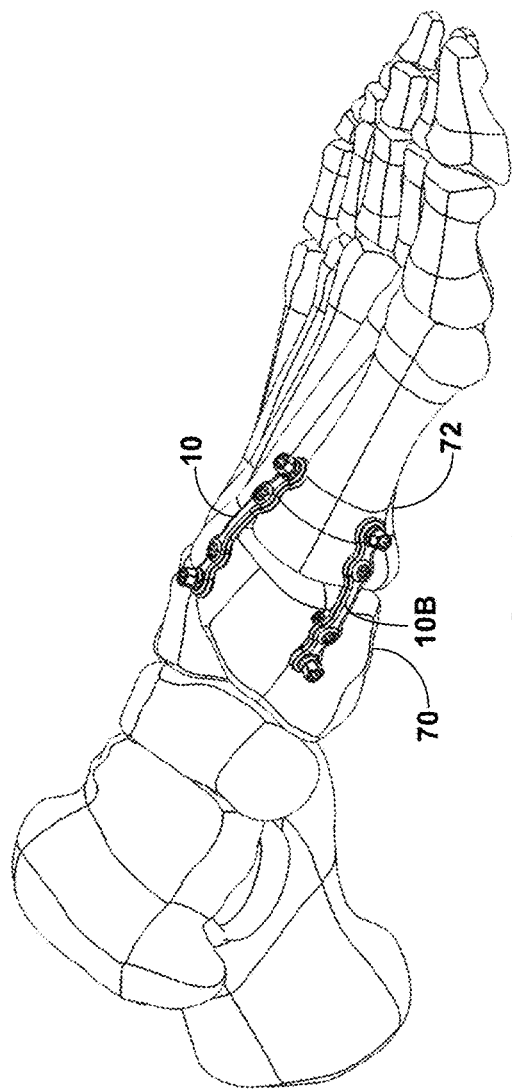

FIG. 21 illustrates bone plate 10B attached on the dorsal side across the tarsometatarsal joint separating medial cuneiform 70 from first metatarsal 72. The bone plate is attached to medial cuneiform 70 and first metatarsal 72 with screws inserted through first and second fixation holes 30, 34 of the bone plate.

Securing a first bone plate 10 with a single screw connecting the bone plate to an underlying bone portion (e.g., metatarsal 72) and then attaching the second bone plate 10B prior to completing attachment of the first bone plate 10 may be useful for a variety of reasons. With only a single screw securing the first bone plate 10 to the bone portion, the bone portion may be further manipulable during installation of the second bone plate 10B. For example, the clinician may be able to pivot metatarsal 72 around the single screw connecting the first bone plate 10 to the metatarsal. This can provide some degree of mobility or freedom for the clinician to adjust the position of the first metatarsal in the transverse plane, frontal plane, and/or sagittal plane prior to or concurrent with attaching the second bone plate 10B. Additionally or alternatively, this arrangement provides mobility to allow the bend 40 in the second bone plate 10B (when so configured) to be deformed to provide additional reinforcing correction of the bone portion (e.g., biasing the metatarsal laterally to close the intermetatarsal angle).

Figure 22:
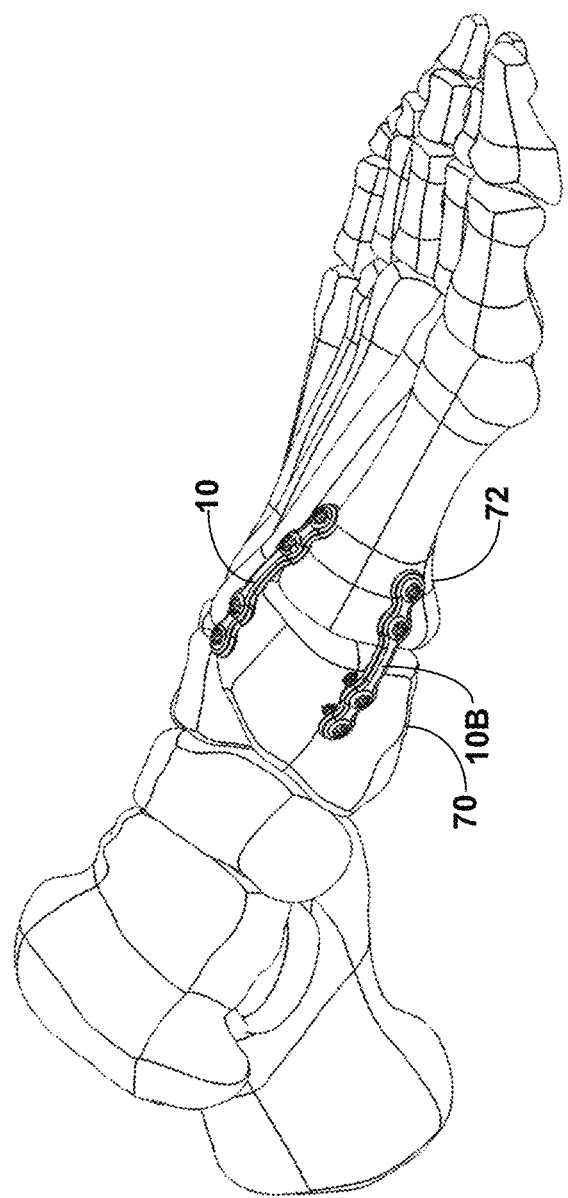

Once second bone plate 10B is attached to medial cuneiform 70 and first metatarsal 72 with screws inserted through first and second fixation holes 30, 34 of the bone plate, the clinician can proceed to complete attachment of the first bone plate 10 and/or second bone plate 10B. For example, the clinician may install screws through third fixation hole 32 and fourth fixation hole 36 of the first bone plate 10 and/or second bone plate 10B into the underlying bones to complete installation as shown in FIG. 22.

It should be appreciated that the foregoing discussion of example procedural steps described in connection with FIGS. 10-22 our exemplary and the procedure may be varied according to disclosure. For example, a clinician may attach a medial bone plate prior to attaching a dorsal bone plate or may only attach a single bone plate. As another example, the clinician may insert an initial driving pin and/or locking screw through a first fixation hole into the first metatarsal 72 instead of the medial cuneiform 70 as discussed in the example. As a still further example, the installation procedure may be modified to incorporate one or more additional fixation elements that can be used in addition to or in lieu of the described bone plating system and techniques. Example additional fixation elements that may be used include, but are not limited to, a lag screw, pin, and/or staple that is inserted across the separation between the two bone portions, such as across the tarsometatarsal joint (e.g., through the first tarsometatarsal joint and into the second metatarsal) and/or a staple that is inserted across the tarsometatarsal joint.

In instances where a bone plating system according to the disclosure is applied to both a dorsal side and a medial side of a metatarsal and cuneiform, the two bone plates may reinforce a realignment introduced during a bone realignment procedure. For example, bone plate attached the dorsal side of the metatarsal and cuneiform may apply an asymmetrically distributed force that is greater on the plantar side of the joint than the dorsal side of the joint, which may have a tendency to plantarflex the metatarsal. The bone plate attached the medial side of the metatarsal and cuneiform may apply an asymmetrically distributed force that is greater on the lateral side of the joint than the medial side of the joint, which may have a tendency to bias the distal end of the metatarsal laterally to close an intermetatarsal angle between the metatarsal to which the bone plate is attached and an adjacent metatarsal.

As described above, bone plate 10 may be positioned over two bone portions to be fixated together with the plate. The bone plate may be positioned over the bone portions in an undeformed state, e.g., prior to compressing bend 40. Once positioned over one or both bone portions, the bone plate can be deformed, for example, by inserting one or more locking screws and/or driving pins or equivalent compressive threaded elements through the fixation hole(s) of the bone plate. This can cause the bend in the bone plate to deform toward a more flattened profile.

In yet additional examples, bone plate 10 with bend 40 may be pre-tensioned (e.g., pre-compressed) before or concurrent with being positioned over a joint between two adjacent bone portions to be fixated. For example, using hand manipulation and/or a bending instrument, bend 40 of the plate may be compressed toward a more planar shape and held in compression while placed spanning the join between the bone portions being fixated. While held in compression, one or more driving pins and/or fixation elements (e.g., screws) can be inserted through the fixation holes of the bone plate into the underlying bone portions.

In these examples, bone plate 10 may have a configuration and may be deformed according to any of the shape profiles and configurations discussed above, albeit with the deformation occurring at least partially prior to attachment of the bone plate to one or both underlying bone portions. In these applications, at least one (and optionally all) fixation elements used to secure the pre-deformed bone plate to the underlying bone portion(s) may be non-locking screws or locking screws configured with a lower compression ratio (e.g., one not effective to substantially deform the plate upon installation, such as compression ratio less than 1.5, or a compression ratio of 1.0). That said, in some implementations, locking screw 50 with an enhanced compression ratio may be installed (e.g., through one or both fixation holes closest to joint 74) to help affix the pre-deformed bone plate to the underlying bone portions.

Figure 23:
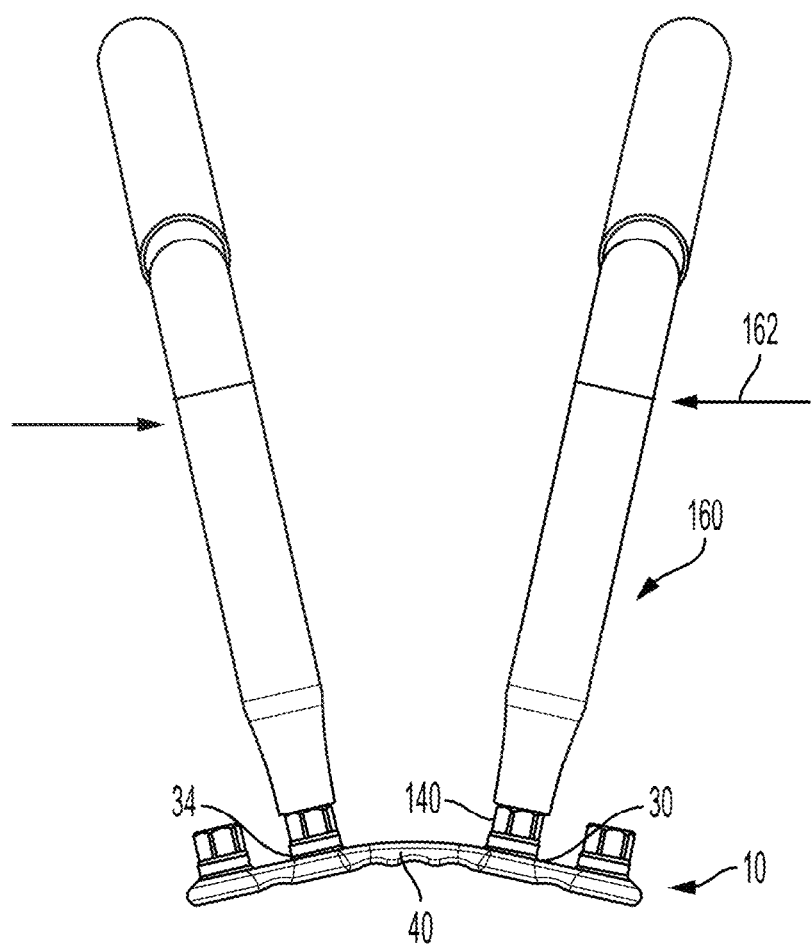
FIGS. 23 and 24 show example procedure steps for pre-tensioning a bone plate prior to installation.
Figure 24:
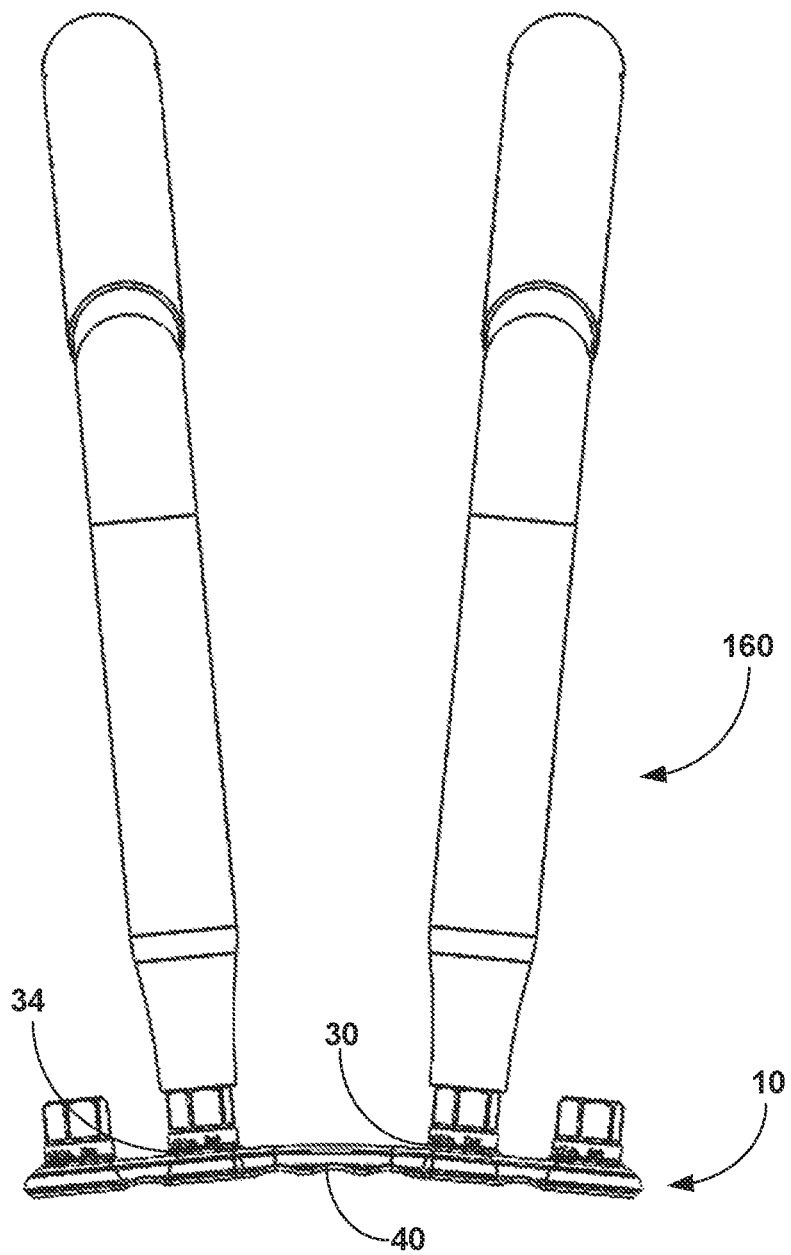

FIGS. 23 and 24 show one example implementation in which an instrument is used to pre-deform bone plate 10 prior to installation. FIG. 23 illustrates bone plate 10 connected to a bending instrument 160 prior to compression which, in the illustrated example, is shown as plate bending arms. The plate bending arms 160 are inserted through drill guides 140 and/or fixation holes of the bone plate on opposite sides of bend 40. The handles can be squeezed together as shown in FIG. 24 to deform the bend in bone plate 40 and pre-compress the bone plate. The handles can be squeezed together in a direction indicated by force vector arrows 162, e.g., with one hand of the clinician grasping both handles and squeezing them together.

Once pre-compressed, the comparatively flat plate can be positioned over the two bone portions to be fixated together and held to one or both bone portions with a driving pin or other fixation feature. Plate bending arms 160 can then be removed, the screw holes prepared, and screws plated through the fixation holes of the plate and into underlying bone.

When bone plate 10 is pre-compressed prior to installation, the screws used to fixate the plate to the underlying bone portions may or may not include a locking screw 50 as described above with comparatively high compression ratio. In some implementations, all the screws utilized to fixate the bone plate to the underlying bone portions may be non-locking screws or locking screw with lower compression ratio.

In some implementations, the components of the bone plate systems described herein (e.g., one or more bone plates, screws and/or other fixation elements) may be provided as part of a kit. The kit may be a disposable single-use surgical kit. The terms "disposable" and "single-use" are meant to convey that the surgical kit, in addition to all components included in the surgical kit, is intended for use on only one surgical patient. After the surgical procedure on the one surgical patient is completed, any components that are not implanted into the one surgical patient can be discarded using conventional methods.

The kit can include a sterile container in which various surgical items can be contained. The container can be sterilized using any appropriate sterilizing means (e.g., exposure to ethylene oxide, steam autoclave, gamma radiation). In one example, the various surgical items can be placed into the container, and the container and the various surgical items included in the container can be sterilized in a single step. The sterile container may be partially or wholly enclosed in a packaging that can serve to protect the container as well as seal and maintain a sterility of the container. The packaging and/or the sterile container can be made of a transparent material, such as an appropriate polymer, to allow viewing of the surgical items included in the container.

The disposable single-use kit can include all or any combination of one or more of the described surgical items. The items to be included in the kit may vary depending on the specific surgical procedure for which the kit is intended to be used. Other embodiments of the kit can include two or more sterile packages with different components in each sterile package. For example, a first sterile package containing the bone plates, fasteners, and pins may be provided along with a second sterile package containing instruments such as plate manipulation and/or bone preparation instruments. Such a kit can also be provided in modular form with components grouped together in separate sterile packages to be selected to provide a complete kit for the desired surgical procedure.

Various examples have been described. These and other examples are within the scope of the following claims.

The invention claimed is:

1. A method of applying a bone plate across a separation between a first bone portion and a second bone portion, the method comprising:
   positioning a bone plate across a separation between a first bone portion and a second bone portion, the bone plate having a first fixation hole, a second fixation hole, and a bend between the first fixation hole and the second fixation hole, wherein positioning the bone plate across the separation comprises positioning the bend over the separation with a gap between a bone-facing surface of the bone plate and the separation;
   inserting a locking screw through the first fixation hole, wherein the locking screw has a head with a head thread and a shaft with a shaft thread, the locking screw has a compression ratio greater than 1.0, and the first fixation hole includes threading for engaging with the head thread;
   screwing the locking screw into the first bone portion under the first fixation hole until the head thread of the locking screw is partially engaged with the threading defined by the first fixation hole; and
   further screwing the locking screw into the first bone portion, thereby deforming the bend in the bone plate toward the separation.

2. The method of claim 1, wherein the first bone portion is a metatarsal or a cuneiform, the second bone portion as an other of the metatarsal or cuneiform, and the separation is a tarsometatarsal joint.

3. The method of claim 1, wherein the first bone portion and the second bone portion are two portions of a metatarsal and the separation is a cut between the two portions.

4. The method of claim 1, wherein the compression ratio of the locking screw is at least 1.5.

5. The method of claim 4, wherein the compression ratio is greater than 1.9.

6. The method of claim 4, wherein the bone plate defines a thickness ranging from 1.0 mm to 2 mm.

7. The method of claim 1, further comprising, prior to screwing the locking screw into the first bone portion, provisionally fixating the first bone portion to the second bone portion by at least inserting a fixation pin through an end face of the first bone portion and into an end face of the second bone portion.

8. The method of claim 1, further comprising inserting a screw through the second fixation hole and screwing the screw into the second bone portion under the second fixation hole.

9. The method of claim 8, wherein:
   the second screw also comprises a head with a head thread and a shaft with a shaft thread, the second screw having a compression ratio greater than 1.0;
   the second fixation hole includes threading for engaging with the head thread of the second screw; and
   screwing the second screw into the second bone portion comprises screwing the second screw until the head thread of the second screw is partially engaged with the threading defined by the second fixation hole, and further screwing the second screw into the second bone portion.

10. The method of claim 1, wherein:
the gap between the bone-facing surface of the bone plate and the separation is at least 1.75 mm, and
further screwing the locking screw into the first bone portion, thereby deforming the bend in the bone plate toward the separation, comprises reducing the gap to a distance less than 1.5 mm.

11. The method of claim 1, wherein deforming the bend in the bone plate toward the separation comprises establishing an asymmetrically distributed load across an end of the first bone portion and an end of the second bone portion, wherein the asymmetrically distributed load has a greater magnitude on a side of the first bone portion and the second bone portion opposite a side against which the bone plate is positioned.

12. The method of claim 1, wherein the bone plate has a length defining a longitudinal axis, the first fixation hole is spaced from the second fixation hole with the first fixation hole on one side of the separation and the second fixation hole on an other side of the separation.

13. The method of claim 12, wherein the bone plate further comprises a third fixation hole positioned between the first fixation hole and a first terminal end of the bone plate and a fourth fixation hole positioned between the second fixation hole and a second terminal end of the bone plate.

14. The method of claim 13, wherein the first fixation hole, the second fixation hole, the third fixation hole, and the fourth fixation hole are co-axial with each other along the longitudinal axis of the bone plate.

15. The method of claim 12, wherein the bone plate further comprises at least one branch extending outwardly from the longitudinal axis of the bone plate to define at least one of a Y-shape, an L-shape, a T-shape, and a U-shape.

16. The method of claim 1, further comprising, prior to inserting the locking screw through the first fixation hole,
screwing a driving pin through the first fixation hole into the first bone portion under the first fixation hole, the driving pin extending from a proximal end to a distal end, and the driving pin including threading adjacent the distal end and an enlarged region having a cross-sectional size larger than a cross-sectional size of the first fixation hole proximal spaced from the distal end,
wherein screwing the driving pin through the first fixation hole comprises screwing the driving pin through the first fixation hole and into the first bone portion under the first fixation hole at least until the enlarged region presses against a top side of the bone plate, thereby deforming the bend in the bone plate toward the separation.

17. The method of claim 1, wherein the bone plate has a length defining a longitudinal axis, the first fixation hole is spaced from the second fixation hole with the first fixation hole on one side of the separation and the second fixation hole on an other side of the separation, and the bone plate further comprises a third fixation hole positioned between the first fixation hole and a first terminal end of the bone plate and a fourth fixation hole positioned between the second fixation hole and a second terminal end of the bone plate.

18. The method of claim 17, further comprising:
inserting a first driving pin through the first fixation hole into the first bone portion,
inserting a second driving pin through the second fixation hole into the second bone portion,
inserting a third driving pin through the third fixation hole into the first bone portion, and
removing the first driving pin from the first fixation hole prior to inserting the locking screw through the first fixation hole, wherein inserting the locking screw through the first fixation hole comprises inserting the locking screw through the first fixation hole with the second driving pin inserted through the second fixation hole and the third driving pin inserted through the third fixation hole.

19. The method of claim 18, wherein the locking screw comprises a first locking screw and further comprising a second locking screw, the second locking screw has a head with a head thread and a shaft with a shaft thread, the second locking screw having a compression ratio greater than 1.0, and the second fixation hole includes threading for engaging with the head thread of the second locking screw; and
further comprising:
inserting the second locking screw through the second fixation hole and screwing the second locking screw into the second bone portion under the second fixation hole until the head thread of the second locking screw is engaged with the threading defined by the second fixation hole; and
after inserting the first locking screw and the second locking screw, inserting a third screw through the third fixation hole into the first bone portion and inserting a fourth screw through the fourth fixation hole into the second bone portion.

20. The method of claim 19, wherein:
the compression ratio of the first locking screw and the second locking screw is each at least 1.5, and
each of the third screw and the fourth screw is a non-locking screw or a locking screw exhibiting a compression ratio less than 1.5.

21. The method of claim 1, wherein the first bone portion is a metatarsal or a cuneiform, the second bone portion as an other of the metatarsal or cuneiform, and the joint is a tarsometatarsal joint, and further comprising, prior to positioning the bone plate across the tarsometatarsal joint:
preparing an end of the metatarsal;
preparing an end of the cuneiform; and
moving the metatarsal in at least the transverse plane to close an intermetatarsal angle between the metatarsal and an adjacent metatarsal.

22. The method of claim 21, wherein positioning the bone plate across the tarsometatarsal joint comprises positioning the bone plate on at least one of a dorsal side and a medial side of the metatarsal and the cuneiform.

23. The method of claim 21, wherein the metatarsal is a first metatarsal and the cuneiform is a medial cuneiform.

24. The method of claim 21, wherein positioning the bone plate across the tarsometatarsal joint comprises positioning a first bone plate on a dorsal side of the tarsometatarsal joint and positioning a second bone plate on a medial side of the tarsometatarsal joint, the first bone plate and the second bone plate each comprising the first fixation hole on one side of the tarsometatarsal joint, the second fixation hole on an other side of the tarsometatarsal joint, a third fixation hole between the first fixation hole and a first terminal end of the bone plate, and a fourth fixation hole positioned between the second fixation hole and a second terminal end of the bone plate.

25. The method of claim 24, wherein:
the first bone plate is installed by inserting the locking screw through one of the first and second fixation holes of the first bone plate and inserting a secondary screw through an other of the first and second fixation holes of the first bone plate, and prior to inserting screws through the third and fourth fixation holes of the first bone plate, the second bone plate is installed by inserting the locking screw through one of the first and second fixation holes of the second bone plate and inserting a secondary screw through an other of the first and second fixation holes of the second bone plate.

26. An orthopedic fixation system comprising:

a bone plate having a length defining a longitudinal axis extending from a proximal end of the body to a distal end of the body, wherein the bone plate has a top surface and a bone-facing surface opposite the top surface, the bone plate includes a first fixation hole extending through the body and a second fixation hole extending through the body, the length of the bone plate is configured to cross a separation with one of the first fixation hole and the second fixation hole positioned over a first bone portion and an other of the first fixation hole and the second fixation hole positioned of a second bone portion, at least the first fixation hole includes threading, and the bone plate includes a bend offsetting a portion of the bone plate between the first fixation hole and the second fixation hole relative portions of the bone plate defining the first fixation hole and the second fixation hole; and a locking screw having a head with a head thread and a shaft with a shaft thread, the locking screw having a compression ratio greater than 1.0, and wherein the locking screw is configured to be inserted through the first fixation hole into at least one of the first bone portion and the second bone portion and the head thread engaged with the threading defined by the first fixation hole, and the compression ratio is effective to cause the bone plate to deform when the head thread is partially engaged with the threading defined by the first fixation hole and the screw is further turned.

27. The system of claim 26, wherein the first bone portion is a metatarsal or a cuneiform, the second bone portion as an other of the metatarsal or cuneiform, and the separation is a tarsometatarsal joint.

28. The system of claim 26, wherein the first bone portion and the second bone portion are two portions of a metatarsal and the separation is a cut between the two portions.

29. The system of claim 26, wherein the compression ratio is greater than 1.5.

30. The system of claim 29, wherein the second fixation hole also includes threading and the locking screw comprises a first locking screw, and further comprising a second locking screw, the second locking screw has a head with a head thread and a shaft with a shaft thread, the shaft thread having a pitch greater than a pitch of the head thread, the compression ratio of the second locking screw is greater than 1.5, and the second locking screw is configured to be inserted through the second fixation hole into the second bone portion and the head thread of the second locking screw engaged with the threading defined by the second fixation hole.

31. The system of claim 26, wherein the bone plate further comprises a third fixation hole positioned between the first fixation hole and a first terminal end of the bone plate and a fourth fixation hole positioned between the second fixation hole and a second terminal end of the bone plate.

32. The system of claim 31, further comprising a third screw configured to be inserted through the third fixation hole and a fourth screw configured to be inserted through the fourth fixation hole, wherein each of the third screw and the fourth screw is a non-locking screw or a locking screw exhibiting a compression ratio less than 1.5.

* * * * *